United States Patent
Branum et al.

(10) Patent No.: US 10,273,165 B1
(45) Date of Patent: Apr. 30, 2019

(54) METHOD AND APPARATUS TO MONITOR AND CONTROL A WATER SYSTEM

(71) Applicant: EVOQUA WATER TECHNOLOGIES LLC, Pittsburgh, PA (US)

(72) Inventors: Scott Branum, Birmingham, AL (US); Erich Hoefferle, Roseville, MN (US)

(73) Assignee: Evoqua Water Technologies LLC, Pittsburgh, PA (US)

(*) Notice: Subject to any disclaimer, the term of this patent is extended or adjusted under 35 U.S.C. 154(b) by 0 days.

(21) Appl. No.: 16/118,112

(22) Filed: Aug. 30, 2018

Related U.S. Application Data

(60) Provisional application No. 62/571,521, filed on Oct. 12, 2017.

(51) Int. Cl.
| | | |
|---|---|---|
| *G06Q 20/14* | (2012.01) | |
| *C02F 1/42* | (2006.01) | |
| *C02F 1/48* | (2006.01) | |
| *C02F 1/00* | (2006.01) | |
| *G06Q 50/06* | (2012.01) | |

(52) U.S. Cl.
CPC ............... *C02F 1/008* (2013.01); *C02F 1/42* (2013.01); *G06Q 20/14* (2013.01); *G06Q 50/06* (2013.01); *C02F 2209/008* (2013.01); *C02F 2209/02* (2013.01); *C02F 2209/03* (2013.01);
(Continued)

(58) Field of Classification Search
CPC .............. C02F 1/008; C02F 1/42–1/427; C02F 2209/008; C02F 2209/02; C02F 2209/05; C02F 2209/005; C02F 2209/03; C02F 2209/40; C02F 2209/44; C02F 2209/445; G06Q 50/06
See application file for complete search history.

(56) References Cited

U.S. PATENT DOCUMENTS

| | | |
|---|---|---|
| 6,696,963 B2 | 2/2004 | Zimmerman et al. |
| 6,753,186 B2 | 6/2004 | Moskoff |
| (Continued) | | |

FOREIGN PATENT DOCUMENTS

| | | |
|---|---|---|
| CN | 103676843 A | 3/2014 |
| CN | 203673315 U | 6/2014 |
| (Continued) | | |

OTHER PUBLICATIONS

U.S. Filter, "Service Deionization Systems Users Guide," Revision C, P91028, Feb. 15, 2000.

*Primary Examiner* — Terry K Cecil

(57) ABSTRACT

A system for providing treated water includes a water treatment unit including an inlet water quality probe, a worker bed, a probe to measure a parameter of water from the worker bed, a polisher bed connected downstream from the worker bed and having a probe to measure a parameter of water from the polisher bed, and a flow meter upstream of the worker bed or downstream of the polisher bed. A controller in communication with the flow meter and the probes is configured to receive data from same. A remote server in communication with the local water treatment unit is configured to receive data from the local water treatment unit. The controller or the server may determine a cumulative flow total, a billing cycle flow total, a current exchange flow total, a contaminant load, or a remaining capacity of the water treatment unit.

13 Claims, 9 Drawing Sheets

(52) U.S. Cl.
CPC ...... *C02F 2209/05* (2013.01); *C02F 2209/40* (2013.01); *C02F 2209/44* (2013.01)

(56) References Cited

U.S. PATENT DOCUMENTS

| | | | |
|---|---|---|---|
| 6,954,701 | B2 | 10/2005 | Wolfe |
| 7,295,919 | B2 | 11/2007 | Humphrey |
| 7,424,399 | B2 | 9/2008 | Kahn et al. |
| 8,180,489 | B2 | 5/2012 | Quinn et al. |
| 8,279,080 | B2 | 10/2012 | Pitchford et al. |
| 8,347,427 | B2 | 1/2013 | Klicpera |
| 8,518,262 | B2 | 8/2013 | Watkins et al. |
| 8,535,540 | B2 | 9/2013 | Chandler, Jr. |
| 8,887,324 | B2 | 11/2014 | Klicpera |
| 8,958,917 | B2 | 2/2015 | Wolfe et al. |
| 9,077,183 | B2 | 7/2015 | Thomas et al. |
| 9,100,728 | B2 | 8/2015 | Higgins et al. |
| 9,460,596 | B1 | 10/2016 | Moses |
| 9,485,530 | B2 | 11/2016 | Diachenko |
| 9,494,480 | B2 | 11/2016 | Klicpera |
| 9,749,792 | B2 | 8/2017 | Klicpera |
| 9,769,420 | B1 | 9/2017 | Moses |
| 9,945,103 | B2 | 4/2018 | Thompson et al. |
| 9,981,868 | B2 * | 5/2018 | Raymont .................. C02F 9/00 |
| 2016/0052798 | A1 | 2/2016 | Downs et al. |
| 2016/0131608 | A1 * | 5/2016 | Howes, Jr. ............. G01N 27/49 |
| | | | 324/693 |
| 2018/0075399 | A1 | 3/2018 | Agarwal et al. |
| 2018/0118580 | A1 | 5/2018 | Park et al. |

FOREIGN PATENT DOCUMENTS

| | | |
|---|---|---|
| CN | 206039258 U | 3/2017 |
| CN | 107055645 A | 8/2017 |
| CN | 206915784 U | 1/2018 |
| CN | 107680274 A | 2/2018 |
| CN | 107808291 A | 3/2018 |
| EP | 2347307 A1 | 7/2011 |
| KR | 101467527 B1 | 12/2014 |
| WO | 2018035358 A1 | 2/2018 |

* cited by examiner

METHOD AND APPARATUS TO MONITOR AND CONTROL A WATER SYSTEM

RELATED APPLICATIONS

This application claims priority under 35 U.S.C. § 119(e) to U.S. Patent Application Ser. No. 62/571,521, titled "METHOD AND APPARATUS TO MONITOR AND CONTROL A WATER SYSTEM", filed on Oct. 12, 2017, which is herein incorporated by reference in its entirety for all purposes.

BACKGROUND

Field of Disclosure

Aspects and embodiments disclosed herein are directed generally to methods and apparatus for monitoring, controlling, and maintaining water treatment systems.

Discussion of Related Art

Flow meters, conductivity and resistivity meters, temperature sensors, pH sensors and hydrogen sulfide sensors, for example, along with other scientific instruments are widely used in many remote locations for a variety of purposes including monitoring the condition of a water purification system. It is often necessary for workmen to physically visit the remote sites to monitor the flow meters or other instruments (e.g., samplers) to gather data. Multiple site visits in numerous locations is a challenging, labor intensive, and expensive task. Ensuring that each site is operational, and that maintenance or service is regularly scheduled provides for obtaining accurate and reliable data.

SUMMARY

In accordance with an aspect of the present disclosure there is provided a system for providing treated water. The system comprises a local water treatment unit including an inlet water quality probe disposed to measure at least one inlet water parameter of feedwater to be treated, the inlet water quality probe including a conductivity sensor and a temperature sensor, a worker bed having ion exchange media contained therein, and disposed to receive the feedwater to be treated, a worker probe disposed to measure at least one worker water parameter of water from the worker bed, the worker probe including a worker conductivity sensor and a worker temperature sensor, a polisher bed having ion exchange media contained therein, and fluidly connected downstream from the worker bed, and a polisher probe disposed to measure at least one polisher water parameter of water from the polisher bed, the polisher probe including a polisher conductivity sensor and a polisher temperature sensor. A flow meter is positioned at least one of upstream of the worker bed and downstream of the polisher bed and is configured to measure flow data of water introduced into the first local water treatment unit. A controller is in communication with the flow meter, the inlet water quality probe, the worker probe, and the polisher probe, the controller configured to receive the flow data from the flow meter, the at least one measured inlet water parameter from the inlet water quality probe, the at least one worker water parameter from the worker probe, and the at least one polisher water parameter from the polisher probe. A server is remote from and in communication with the local water treatment unit, the server configured to receive from the local water treatment unit, at least one of the flow data, the at least one measured inlet water parameter, the at least one worker water parameter, and the at least one polisher water parameter. At least one of the controller and the server is further configured to determine at least one of a cumulative flow total based on an aggregate of the flow data, a billing cycle flow total based on the flow data during a billing cycle through the local water treatment unit, a current exchange flow total based on the flow data during a current service period of the worker bed, a contaminant load based on the at least one inlet water parameter, and a remaining capacity of the local water treatment unit based at least on the contaminant load.

In some embodiments, the system further comprises a second local water treatment unit including a second inlet water quality probe disposed to measure at least one inlet water parameter of a second feedwater to be treated in the second local water treatment unit, the second inlet water quality probe including a second conductivity sensor and a second temperature sensor, a second worker bed having ion exchange media contained therein, and disposed to receive the second feedwater to be treated, a second worker probe disposed to measure at least one water parameter of water from the second worker bed, the second worker probe including a second worker conductivity sensor and a second worker temperature sensor, a second polisher bed having ion exchange media contained therein, and fluidly connected downstream from the second worker bed, and a second polisher probe disposed to measure at least one polisher water parameter of water from the second polisher bed, the second polisher probe including a second polisher conductivity sensor and a second polisher temperature sensor. A second flow meter is positioned at least one of upstream the second worker bed and downstream of the second polisher bed and configured to measure flow data of water introduced into the second local water treatment unit. A second controller is in communication with the second flow meter, the second inlet water quality probe, the second worker probe, and the second polisher probe, the second controller configured to receive the flow data from the second flow meter, the at least one measured inlet water parameter from the second inlet water quality probe, the at least one worker water parameter from the second worker probe, and the at least one polisher water parameter from the second polisher probe.

In some embodiments, the second water treatment unit is remote from and in communication with the server, the server further configured to receive from the second local water treatment unit, at least one of the flow data from the second flow meter, the at least one measured inlet water parameter from the second inlet water quality probe, the at least one worker water parameter from the second worker probe, and the at least one polisher water parameter from the second polisher probe.

In some embodiments, one of the second controller and the server is configured to determine at least one of a cumulative flow total of the second water treatment unit based on an aggregate of the flow data through the water second water treatment unit, a second billing cycle flow total based on the flow data during a second billing cycle through the second water treatment unit, a current exchange flow total based on the flow data during a current service period of the second worker bed, a second contaminant load based on the at least one inlet water parameter of the second feedwater, and a remaining capacity of the second local water treatment unit based at least on the second contaminant load.

In some embodiments, the local water treatment unit further includes an inlet pressure sensor disposed to monitor a pressure of the feedwater to the water treatment unit and an outlet pressure sensor disposed to monitor a pressure of the treated water from the water treatment unit, and wherein the controller is further configured to receive inlet pressure data from the inlet pressure sensor and outlet pressure data from the outlet pressure sensor and generate an alarm if a difference in the pressure of the feedwater relative to the pressure of the treated water is above a differential pressure setpoint. In still other embodiments, the water treatment unit further includes a pre-filter, or an upstream filtration unit operation, such as a bag filter, disposed upstream of the ion exchange media in the water treatment unit. The first inlet pressure sensor can be, in such still other embodiments, disposed upstream of the pre-filter and the outlet pressure sensor can be disposed downstream from the pre-filter. The controller can thus be further configured to receive the pressure data and generate an alarm if the difference across the pre-filter is above a predetermined upper value or below a predetermined lower value.

In some embodiments, the local water treatment unit further includes a leak detect module disposed to detect if a leak or moisture from the treatment unit, and wherein the controller is further configured to generate an indication if the leak detection module detects moisture in the enclosure. In some embodiments, the leak detect module includes a sensor disposed externally or outside of but proximate the enclosure of the unit but on a floor upon which the water treatment unit is set.

In some embodiments, the controller further comprises a Bluetooth® interface operatively configured to wirelessly transmit data over a personal area network.

In accordance with another aspect, there is provided a method for providing treated water for a predetermined period of time. The method comprises treating water in a water treatment unit during the predetermined period of time to produce treated water, during the predetermined period of time, measuring a volume of the provided treated water utilizing a sensor positioned in the water treatment unit, during the predetermined period of time, monitoring a parameter of water to be treated in the water treatment unit utilizing a water quality sensor positioned in the water treatment unit, calculating a difference between the measured volume of the provided treated water during the predetermined period of time and a baseline volume of treated water to be provided during the predetermined period of time, and determining a fee adjustment for providing the treated water based on the calculated difference between the measured volume of the provided treated water and the baseline volume of treated water to be provided.

In some embodiments, the method further comprises predicting a remaining service life of the water treatment unit based on at least one of the measured volume of the provided treated water provided during the predetermined period of time and the monitored parameter, and wherein the monitored parameter relates to a conductivity of the water to be treated.

In some embodiments, the method further comprises determining a cumulative volume of treated water provided by the water treatment unit, and determining a remaining service life of the water treatment unit based at least on the cumulative volume of treated water and on the monitored parameter during the predetermined period of time.

In some embodiments, the method further comprises determining a cumulative volume of treated water provided by the water treatment unit, and determining a remaining service life of the water treatment unit based at least on the cumulative volume of treated water and a treatment capacity of the water treatment unit.

In some embodiments, the method further comprises scheduling service of the water treatment unit if the remaining service life is less than a service-initiating life of the water treatment unit.

In some embodiments, the method further comprises calculating an average of the value of the monitored parameter of the water to be treated during the predetermined period of time and utilizing the average value of the monitored parameter as the actual value of the monitored parameter in the act of determining the fee adjustment.

In some embodiments, the method further comprises monitoring a parameter of the provided treated water, and, if the monitored parameter of the provided treated water is outside of a desired range, performing at least one of: generating an alarm, sending a notification to a user, and scheduling service of the water treatment unit.

In some embodiments, the method further comprises monitoring pressure across the water treatment unit and initiating service of the water treatment unit if the monitored pressure exceeds a predetermined differential pressure limit.

In some embodiments, the method further comprises making data indicative of one or more of: cumulative volume of water to be treated during the predetermined period of time, expected volume of water to be treated during the predetermined period of time, parameter of the water to be treated during the predetermined period of time, and expected value of the parameter of the water to be treated during the predetermined period of time available via a web portal.

In some embodiments, the method further comprises determining a schedule for service of the water treatment unit without input from a user of the treated water.

In some embodiments, the method further comprises transmitting data indicative of the volume of the water to be treated and data indicative of the value of the monitored parameter of the water to be treated to a central server remote from the water treatment unit.

In some embodiments, monitoring the parameter of water to be treated comprises monitoring a conductivity of the water to be treated.

In accordance with another aspect, there is provided method for providing treated water over a first predetermined period of time. The method comprises directing a first feedwater to be treated through a first water treatment unit to produce a first treated water, the first water treatment unit including ion exchange media, during the first predetermined period of time, monitoring a parameter of the first feedwater, during the first predetermined period of time, monitoring at least one of a volume of the first feedwater directed through the water treatment unit and the first treated water, transmitting to a server disposed remotely from the first water treatment unit, data indicative of at least one of the volume of the first feedwater and the volume of the first treated water, and data indicative of the monitored parameter, determining a base fee for providing the first treated water during the first predetermined period of time based on at least one of an expected volume of the first feedwater to be treated during the first predetermined period of time and an expected value of the parameter of the water to be treated during the first predetermined period of time, and determining a fee adjustment based on the base fee and a difference between the monitored volume of the first feedwater and the expected volume of the first feedwater to be treated.

In some embodiments, the method further comprises directing a second feedwater to be treated through a second water treatment unit to produce a second treated water, the second water treatment unit disposed remotely from the first water treatment unit and including ion exchange media, during a second predetermined period of time, monitoring a parameter of the second feedwater, during the second predetermined period of time, monitoring at least one of a volume of the second feedwater directed through the second water treatment unit and a volume of the second treated water, transmitting to the server disposed remotely from the second water treatment unit, data indicative of at least one of the volume of the second feedwater and the volume of the second treated water, and data indicative of the monitored parameter of the second feedwater, determining a second base fee for providing the second treated water during the predetermined period of time based on at least one of an expected volume of the second feedwater to be treated and an expected value of the parameter of the second feedwater to be treated during the second predetermined period of time, and determining a second fee adjustment based on the second base fee and a difference between the monitored volume of the second feedwater and the expected volume of the second feedwater to be treated.

In some embodiments, the monitored parameter of the first feedwater represents a conductivity of the first feedwater, and wherein determining the fee adjustment is further based on a difference between the conductivity of the first feedwater and an expected conductivity of the first feedwater.

In some embodiments, the monitored parameter of the second feedwater represents a conductivity of the second feedwater, and wherein determining the second fee adjustment is further based on a difference between the conductivity of the second feedwater and an expected conductivity of the second feedwater.

In some embodiments, the method further comprises determining a remaining treatment capacity of the first water treatment unit based on at least one of a cumulative volume of the first feedwater and the conductivity of the first feedwater directed through the first water treatment unit during the first predetermined period of time.

In some embodiments, the method further comprises determining a remaining treatment capacity of the second water treatment unit based on at least one of a cumulative volume of the second feedwater and the conductivity of the second feedwater directed through the second water treatment unit during the second predetermined period of time.

In accordance with another aspect, there is provided a method of remotely monitoring water treatment units. The method comprises receiving at a remote central server, data from a first water treatment unit that produces a first treated water delivered to a first facility, the central server disposed remotely from the first local facility, the data representative of at least one of a volume of a first feedwater to be treated in the first water treatment unit, a volume of the first treated water, and a conductivity of the first feedwater, during a first predetermined period, receiving at the remote central server, data from a second water treatment unit that produces a second treated water delivered to a second facility that is disposed remotely from the first facility, the central server disposed remotely from the second facility, the data representative of at least one of a volume of a second feedwater to be treated in the second water treatment unit, a volume of the second treated water, and a conductivity of the second feedwater, during a second predetermined period, determining a first base fee for providing the first treated water over the first predetermined period based on at least one of an expected volume of the first feedwater to be treated and an expected value of the conductivity of the first feedwater, determining a second base fee for providing the second treated water over the second predetermined period based on at least one of an expected volume of the second feedwater to be treated and an expected value of the conductivity of the second feedwater, determining a first fee adjustment for providing the first treated water based on the first base fee and a difference between an actual and the expected volume of the first feedwater, and determining a second fee adjustment for providing the second treated water based on the second base fee and a difference between an actual and the expected volume of the second feedwater.

In some embodiments, the method further comprises determining a remaining treatment capacity of the first water treatment unit based on at least one of a cumulative volume of the first feedwater and the conductivity of the first feedwater directed through the first water treatment unit.

In some embodiments, the method further comprises determining a remaining treatment capacity of the second water treatment unit based on at least one of a cumulative volume of the second feedwater and the conductivity of the second feedwater directed through the second water treatment unit.

In some embodiments, the method further comprises initiating a first service requirement for the first water treatment unit based on a cumulative volume of the first feedwater treated in the first treatment unit.

In some embodiments, determining the first fee adjustment is further based on the conductivity of the first feedwater during the first predetermined period.

In some embodiments, the method further comprises initiating a second service requirement for the second water treatment unit based on a cumulative volume of the second feedwater treated in the second treatment unit.

In some embodiments, determining the second fee adjustment is further based on the conductivity of the second feedwater during the second predetermined period.

In some embodiments, the method further comprises generating a route for a service provider to service the first water treatment unit and the second water treatment unit based at least in part on locations of each of the first facility and the second facility.

In accordance with another aspect there is provided a non-transitory computer readable media having instructions encoded therein which, when executed by a computer, cause the computer to perform any one of the methods disclosed above.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
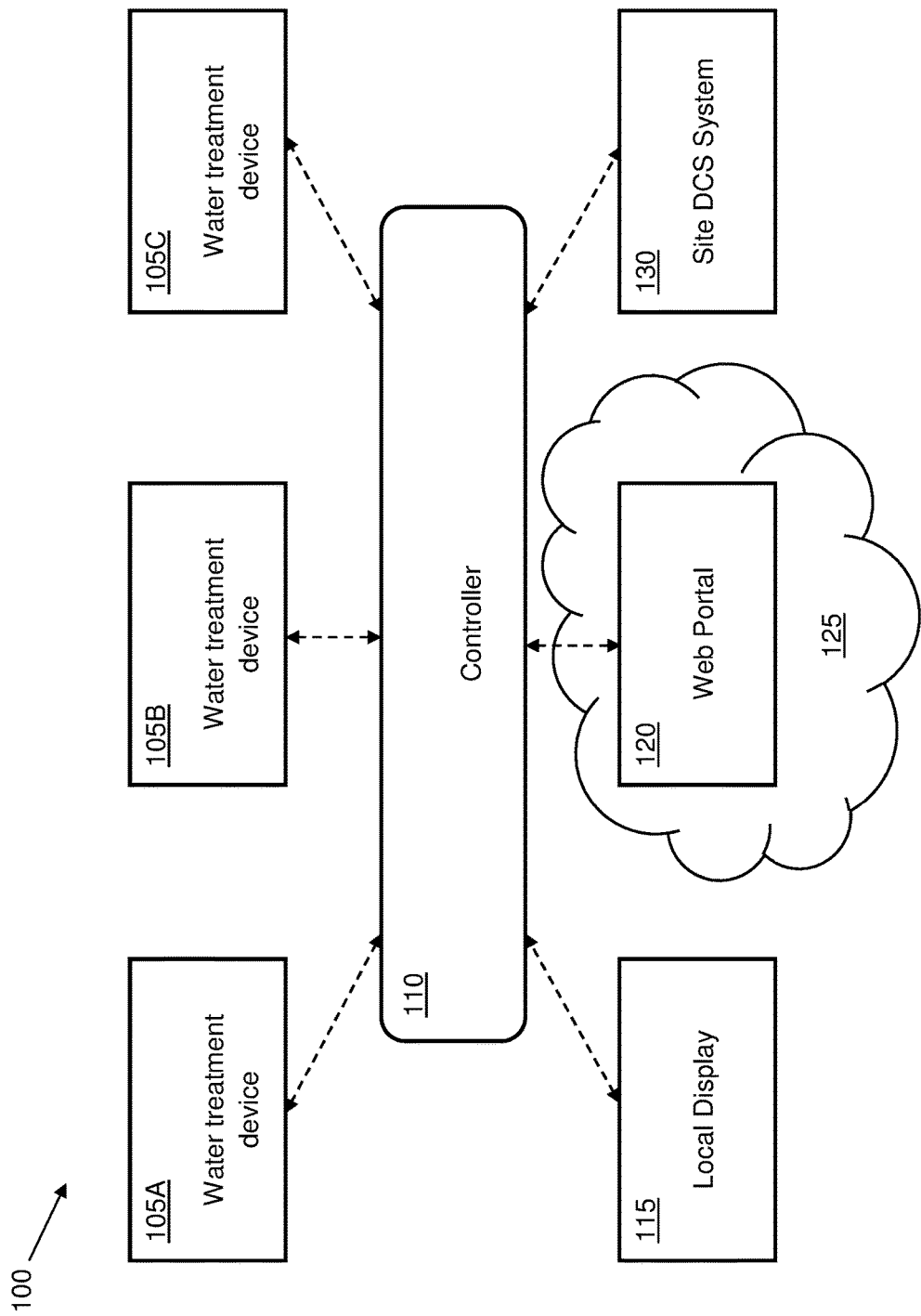
FIG. 1A is a schematic illustration of a water treatment system and associated monitoring system.

Aspects and embodiments disclosed herein are not limited to the details of construction and the arrangement of components set forth in the following description or illustrated in the drawings. Aspects and embodiments disclosed herein are capable of other embodiments and of being practiced or of being carried out in various ways.

Aspects and embodiments disclosed herein include a wireless monitoring system which enables data collection from and monitoring of the status of various meters, sensors, and scientific instruments at one or more locations. The data may be gathered wirelessly, for example, by means of the GSM cellular telephone network using a modem connected to a computer or a hand-held device, by Wi-Fi, or other wireless data collection methods known in the art, e.g., based on the LTE Cat 1, LTE Cat M1 or Cat NB1 standard. In other embodiments, data may be gathered from the monitoring system via a wired connection to a centralized monitoring system.

Aspects and embodiments of a wireless monitoring system may be utilized in the environment of a water treatment system. The water treatment system may include one or more unit operations. The one or more unit operations may include one or more pressure-driven water treatment devices, for example, membrane filtration devices such as nanofiltration (NF) devices, reverse osmosis (RO) devices, hollow fiber membrane filtration devices, etc., one or more ion-exchange water treatment devices, one or more electrically-driven water treatment devices, for example, electrodialysis (ED) or electrodeionization (EDI) devices, one or more chemical-based water treatment devices, for example, chlorination or other chemical dosing devices, one or more carbon filters, one or more biologically-based treatment devices, for example, aerobic biological treatment vessels, anaerobic digesters, or biofilters, one or more radiation-based water treatment devices, for example, ultraviolet light irradiation systems, or other water treatment devices or systems known in the art.

The water treatment system may be utilized to treat water for industrial uses, for example, for use in semiconductor processing plants, food processing or preparation sites, for use in chemical processing plants, to produce purified water for use as lab water, or may be utilized to provide a site with water suitable for irrigation or drinking water purposes. In other embodiments, the water treatment system may be utilized to treat wastewater from industrial or municipal sources.

The water treatment system may include one or more sensors, probes, or instruments for monitoring one or more parameters of water entering or exiting any one or more of the one or more unit operations. The one or more sensors, probes, or instruments may include, for example, flow meters, water level sensors, conductivity meters, resistivity meters, chemical concentration meters, turbidity monitors, chemical species specific concentration sensors, temperature sensors, pH sensors, oxidation-reduction potential (ORP) sensors, pressure sensors, or any other sensor, probe, or scientific instrument useful for providing an indication of a desired characteristic or parameter of water entering or exiting any one or more of the one or more unit operations.

A monitoring system may be utilized to gather data from sensors, probes, or scientific instruments included in the water treatment system and may provide the gathered data to operators local to the water treatment system or to persons, for example, a water treatment system service provider, remote from the water treatment and monitoring system.

Figure 1B:
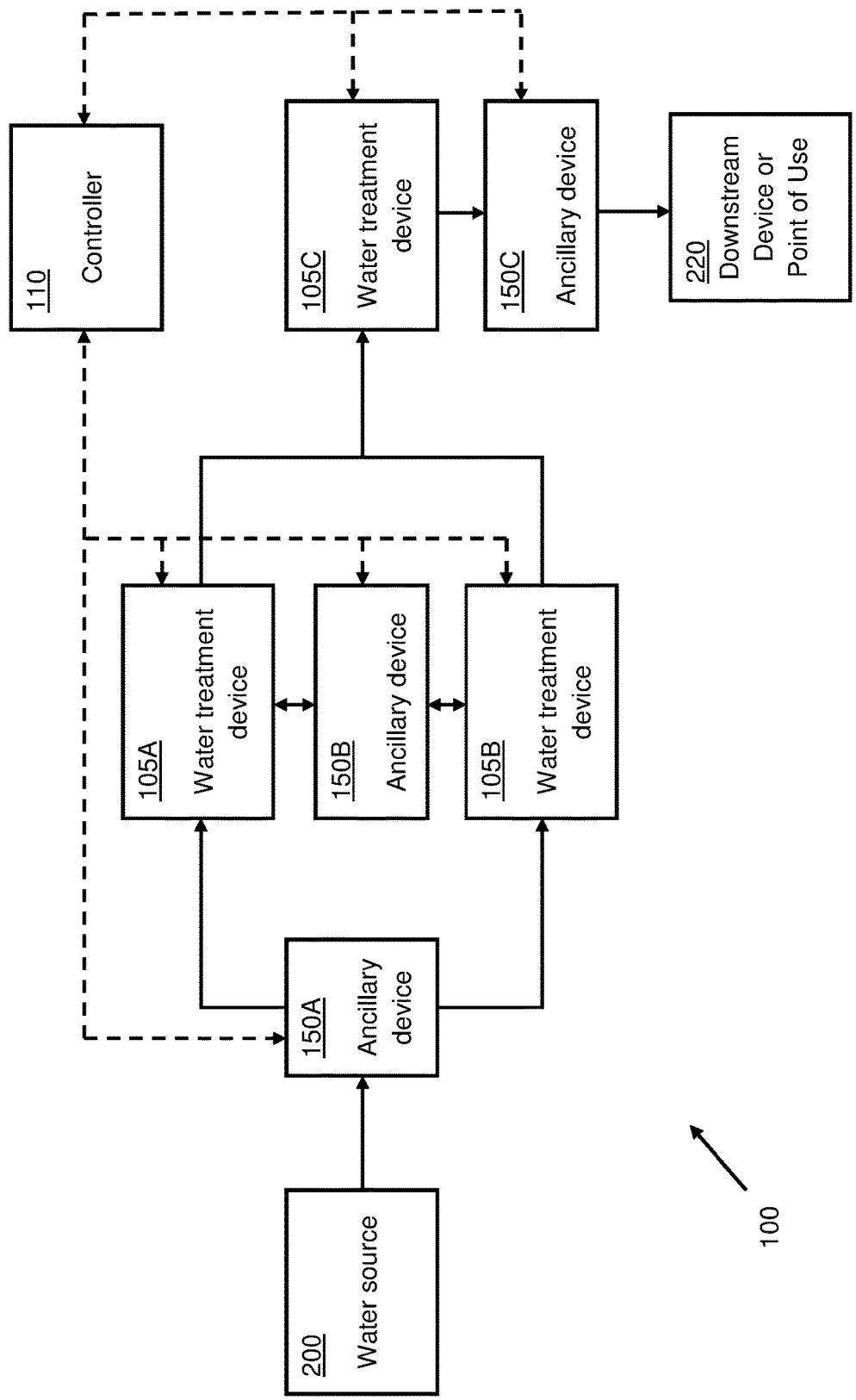
FIG. 1B is a schematic illustration of a water treatment system.

One embodiment of a water treatment system (also referred to herein as a water treatment unit) and associated monitoring system is illustrated schematically in FIG. 1A generally at 100. The water treatment system may include one or more water treatment units or devices 105A, 105B, 105C. The one or more water treatment devices may be arranged fluidically in series and/or in parallel as illustrated in FIG. 1B. Although only three water treatment devices 105A, 105B, 105C are illustrated, it is to be understood that the water treatment system may include any number of water treatment units or devices.

The water treatment system 100 may further include one or more ancillary systems 150A, 150B, 150C, for example, pumps, pre or post filters, polishing beds, heating or cooling units, sampling units, power supplies, or other ancillary equipment fluidically in line with or otherwise coupled to or in communication with the one or more water treatment units 105A, 105B, 105C. The ancillary systems are not limited to only three ancillary systems but may be any number and type of ancillary systems desired in a particular implementation. The one or more water treatment units 105A, 105B, 105C and ancillary systems 150A, 150B, 150C may be in communication with a controller 110, for example, a computerized controller, which may receive signals from and/or send signals to the one or more water treatment devices 105A, 105B, 105C and ancillary systems 150A, 150B, 150C to monitor and control same. The one or more water treatment devices 105A, 105B, 105C and ancillary systems 150A, 150B, 150C may send or receive data related to one or more operating parameters to or from the controller 110 in analog or digital signals. The controller 110 may be local to the water treatment system 100 or remote from the water treatment system 100 and may be in communication with the components of the water treatment system 100 by wired and/or wireless links, e.g., by a local area network or a data bus. A source of water to be treated 200 may supply water to be treated to the water treatment system 100. The water to be treated may pass through or be treated in any of the water treatment devices 105A, 105B, 105C and, optionally, one or more of the ancillary systems 150A, 150B, 150C and may be output to a downstream device or point of use 220.

Returning to FIG. 1A, one or more sensors, probes, or scientific instruments associated with each of the water treatment devices 105A, 105B, 105C may be in communication, via a wired or a wireless connection, to a controller 110 which may include, for example, a local monitoring and data gathering device or system. The one of more sensors, probes or scientific instruments associated with each of the water treatment devices 105A, 105B, 105C may provide monitoring data to the controller 110 in the form of analog or digital signals. The controller 110 may provide data from the sensors or scientific instruments associated with each of the water treatment devices 105A, 105B, 105C to different locations. One of the locations may optionally include a display 115 local to one of the water treatment devices 105A, 105B, 105C or the site at which the water treatment devices 105A, 105B, 105C are located. Another of the locations may be a web portal 120 which may be hosted in a local or remote server or in the cloud 125. Another of the locations optionally may be a distributed control system (DCS) 130 which may be located at the site or at the facility at which the water treatment devices 105A, 105B, 105C are located.

Processing of the data from the one or more sensors, probes, or scientific instruments associated with each of the water treatment devices 105A, 105B, 105C may be performed at the controller 110 and summarized data may be provided to one or more of the locations 115, 120, 130, or the controller 110 may pass raw data from the one or more sensors or scientific instruments or probes to one or more of the locations 115, 120, 130. The data may be available through one or more of the locations 115, 120, 130 to an operator of the water treatment system or any of the individual water treatment devices, to a user of treated water provided by the water treatment system, to a vendor or service provider that may be responsible for maintenance of one or more of the water treatment devices 105A, 105B, 105C or the system 100 as a whole, or to any other interested parties. For example, a user of the water treatment system 100 may access data related to water quality and/or quantity of treated water produced in the water treatment system 100 via the web portal 120 or via the site DCS system 130. The user may utilize such data for auditing purposes or to show compliance with regulations associated with production of the treated water. Further optional configurations contemplate storage of the raw or processed data or both at one or more data storage devices, at any of locations 110, 120 and 130.

Figure 2:
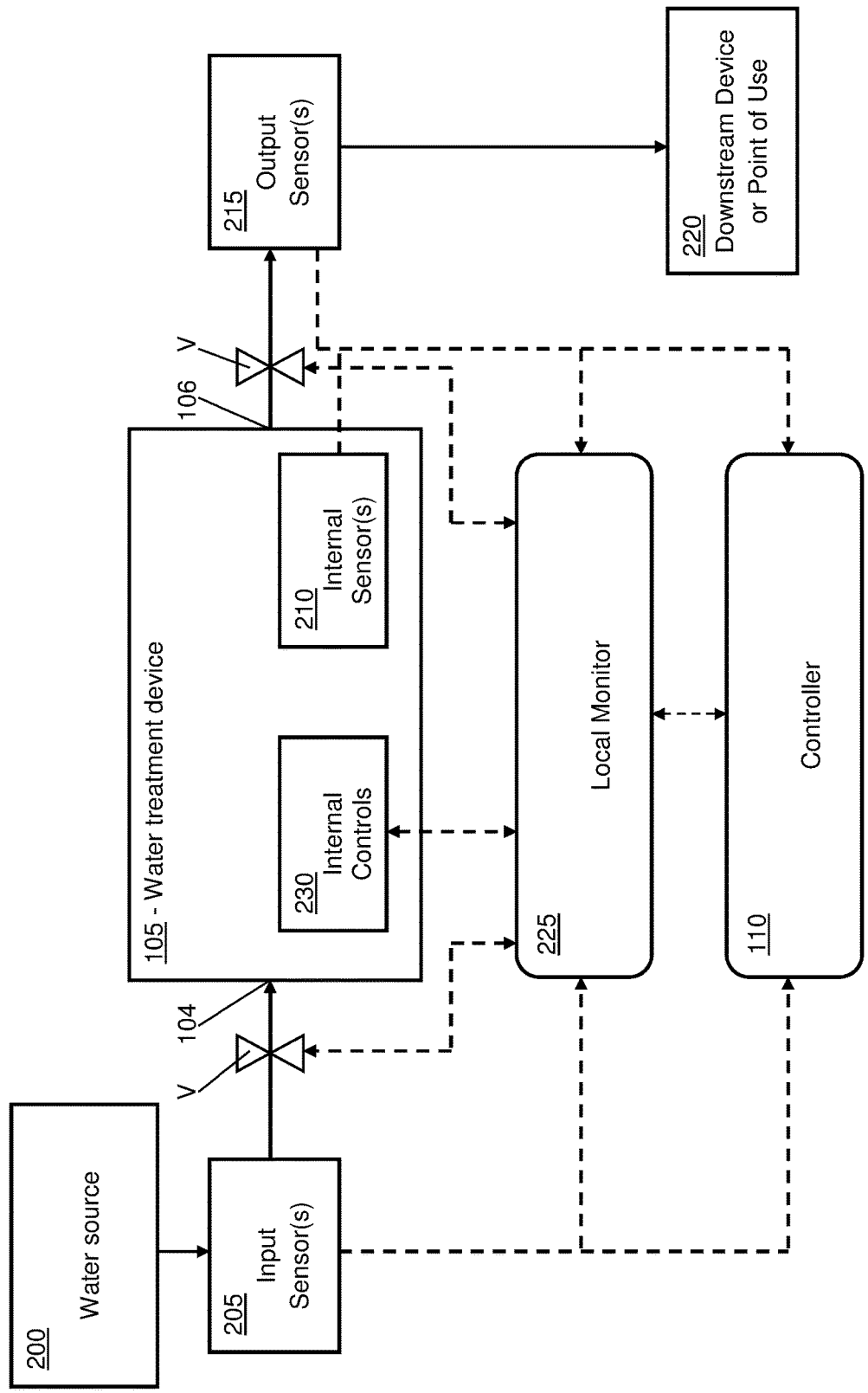
FIG. 2 is a schematic illustration of a water treatment system and associated monitoring system.

Features associated with the water treatment devices 105A, 105B, 105C are illustrated in FIG. 2, wherein an example of a water treatment device (which may be any one or more of water treatment devices 105A, 105B, 105C) is indicated at 105. A source 200 of water (alternatively referred to herein as feedwater) to be treated in the water treatment device 105 may be disposed in fluid communication upstream of the water treatment device 105. The source 200 may be a source of untreated water, water output from a plant or from a point of use at the site at which the water treatment device 105 is located, or an upstream water treatment device. The water to be treated may pass through or otherwise be monitored by one or more sensors 205 upstream of the inlet of the water treatment device 105. The one or more sensors 205 may include, for example, a flow meter, a conductivity sensor, a pH sensor, a turbidity sensor, a temperature sensor, a pressure sensor, an ORP sensor, or any one or more of the other forms of sensors described above. The one or more sensors 205 may provide data regarding one or more measured parameters of the water to be treated in the water treatment device 105 to a local monitor 225 associated with the water treatment device 105 which may pass the data on to the controller 110. The one or more sensors 205 may provide the data in either analog signals or digital signals. The local monitor 225 may be included as hardware or software in the controller 110 or may be a separate device. The one or more sensors 205 may additionally or alternatively provide data regarding the one or more measured parameters of the water to be treated in the water treatment device 105 directly to the controller 110.

The water to be treated may enter the water treatment device 105 through an inlet 104 of the water treatment device 105 and undergo treatment within the water treatment device 105. One or more sensors 210 may be disposed internal to the water treatment device 105 to gather data related to operation of the water treatment device 105 and/or one or more parameters of the water undergoing treatment in the water treatment device 105. The one or more sensors 210 may include, for example, a pressure sensor, level sensor, conductivity sensor, pH sensor, OPR sensor, current or voltage sensor, or any one or more of the other forms of sensors described above. The one or more sensors 210 may provide data related to operation of the water treatment device 105 and/or one or more parameters of the water undergoing treatment in the water treatment device 105 to the local monitor 225, which may pass the data on to the controller 110. The one or more sensors 210 may additionally or alternatively provide data related to operation of the water treatment device 105 and/or one or more parameters of the water undergoing treatment in the water treatment device 105 directly to the controller 110. Communications between the one or more sensors 210 and local monitor 225 and/or controller 110 may be via a wired or wireless communications link.

After treatment in the water treatment device 105 the treated water may exit though an outlet 106 of the water treatment device 105. One or more parameters of the treated water may be tested or monitored by one or more downstream sensors 215. The one or more sensors 215 may include, for example, a flow meter, a conductivity sensor, a pH sensor, a turbidity sensor, a temperature sensor, a pressure sensor, an ORP sensor, or any one or more of the other forms of sensors described above. The one or more sensors 215 may provide data regarding one or more measured parameters of the treated water to the local monitor 225, which may pass the data on to the controller 110. The one or more sensors 215 may additionally or alternatively provide data regarding the one or more measured parameters of the treated water directly to the controller 110. Communications between the one or more sensors 215 and local monitor 225 and/or controller 110 may be via a wired or wireless communications link.

The local monitor 225 may include functionality for controlling the operation of the water treatment device 105. Based on measured parameters of the water to be treated or the treated water from the sensors 205 and/or 215, measured parameters from the one or more internal sensors 210, or based on a command received from an operator, the local monitor 225 may control inlet or outlet valves V (or one or more ancillary systems 150A, 150B, 150C illustrated in FIG. 1B) to adjust a flow rate or residence time of water within the water treatment device 105. The local monitor 225 may also control one or more internal controls 230 of the water treatment device 105 to adjust one or more operating parameters of the water treatment device 105, for example, internal temperature, pressure, pH, electrical current or voltage (for electrically-based treatment devices), aeration, mixing speed or intensity, or any other desired operating parameter of the water treatment device 105.

The local monitor 225 and/or controller 110 may monitor signals from one or more of the input sensors 205, internal sensors 210, and output sensors 215 to determine if an error condition or unexpected event has occurred and may be configured to generate and error message or signal in response to detecting same. For example, in instances in which the input sensors 205 and output sensors 215 include inlet and outlet pressure sensors, the local monitor 225 and/or controller 110 may be configured to receive inlet pressure data from the inlet pressure sensor and outlet pressure data from the outlet pressure sensor and generate an alarm if a difference in the pressure of the feedwater relative to the pressure of the treated water is above a differential pressure setpoint. In instances in which one or more of the input sensors 205, internal sensors 210, and output sensors 215 include a leak detection module disposed to close if moisture is detected in an enclosure of the water treatment unit 105, the local monitor 225 and/or controller 110 may be configured to generate an indication if the leak detection module detects moisture in the enclosure. In some embodiments, the leak detect module includes a sensor disposed externally or outside of but proximate the enclosure of the unit on a floor upon which the water treatment unit is set.

Figure 3:
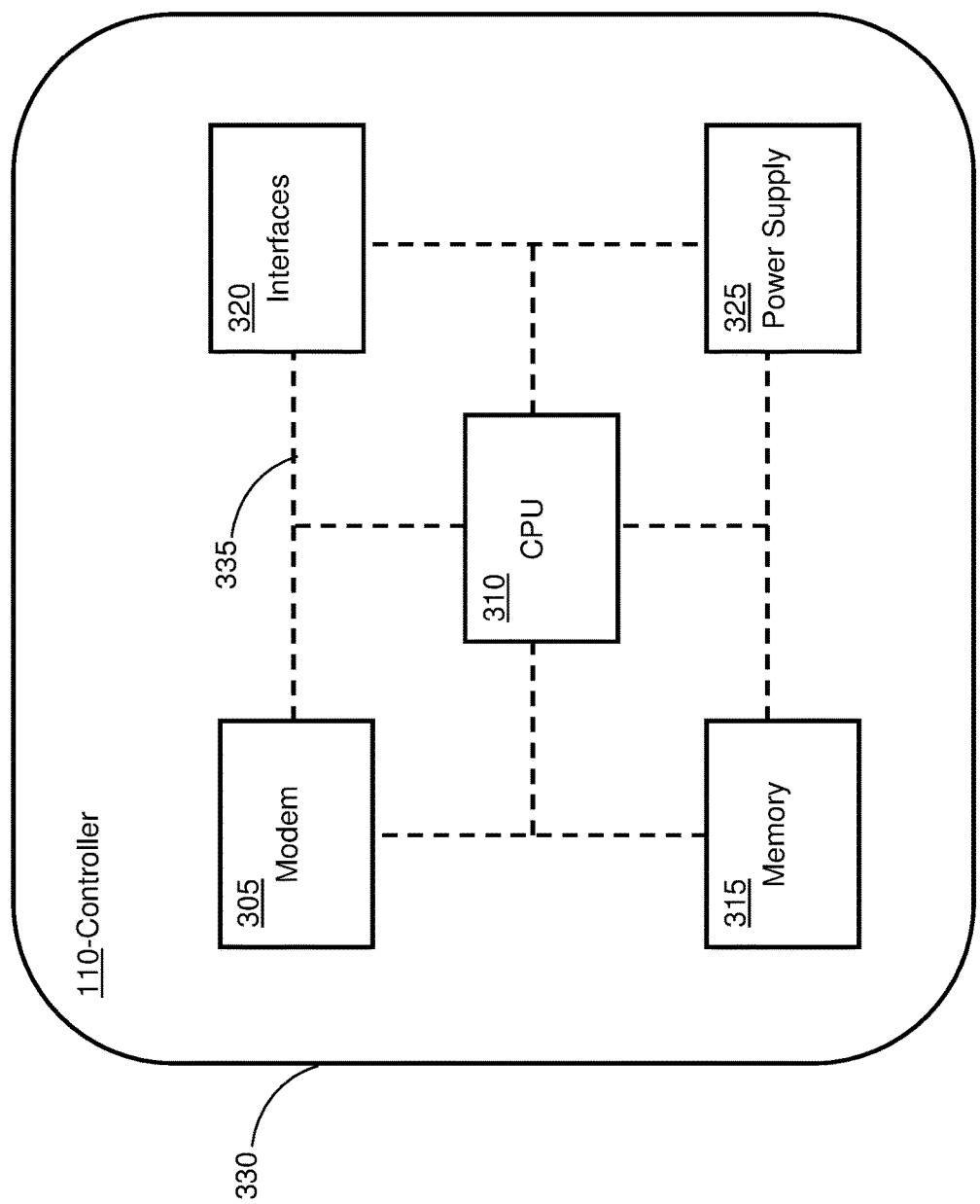
FIG. 3 is a schematic illustration of a data platform/monitoring system for a water treatment system.

In one embodiment, the monitoring system, represented by the controller 110 and illustrated in further detail in FIG. 3, may include one or more of a wireless modem 305 which may, for example, utilize a cellular phone network, e.g., based on the LTE Cat 1, LTE Cat M1 or Cat NB1 standard, to communicate data regarding operation of a water treatment device 105 and/or water to be treated and/or water after being treated in a water treatment device 105 with a remote server or one of locations 115, 120, 130, a processing unit (CPU) 310 operatively connected to the modem 305, a memory 315 operatively connected to the CPU 310 which may be used to store data received from sensors associated with the water treatment devices and/or code for controlling the operation of one or more water treatment devices, one or more interfaces 320, which may include wired or wireless (e.g., Wi-Fi, Bluetooth®, cellular, etc.) interfaces for connecting one or more scientific instruments or any of sensors 205, 210, 215 or other sensors associated with a water treatment device 105 or system to the central processing unit, a power supply 325 for providing electrical power to the modem 305 and the central processing unit, and an enclosure 330 for housing the components at the location. In some embodiments, the one or more interfaces 320 may include a Bluetooth® interface operatively configured to wirelessly transmit data over a personal area network. Any or all of the components of the controller 110 may be communicatively coupled with one or more internal busses 335. In some embodiments, the memory 315 may include a non-transitory computer readable medium including instructions, that when executed by the CPU 310, cause the CPU 310 to perform any of the methods disclosed herein.

A variety of monitoring devices such as a flow meter or other scientific instrument are normally operably connected to the CPU 310 such that data from the monitoring device or scientific instrument is transmitted to the modem 305 where it can be accessed from a remote location through, for example, the cellular phone network.

In one aspect of the disclosure, a remote monitoring and control system architecture is used as illustrated in FIG. 1A. A controller 110 comprising a modem 305 (FIG. 3) and cellular connectivity is connected to various devices, for example, one or more sensors (for example, any one or more of sensors 205, 210, 215) associated with water treatment devices 105A, 105B, and 105C. The one or more sensors may comprise a service deionization tank resistivity monitor, a series of sensors and monitors such as a flow meter, conductivity meter, temperature and pH sensors for a water purification system such as a reverse osmosis system, or the one or more sensors may comprise a series of unit operations combined into a complete system. The information from the various one or more sensors is uploaded to internal portals from the operating business and can also be uploaded to customer portals and customer DCS systems 130. The entire network may be cloud based.

One example of a local water treatment system or unit 100 that may be included in aspect and embodiments disclosed herein is a service deionization system. One example of a local water treatment system or unit 100 including a service deionization system is illustrated generally at 400 in FIG. 4. Water to be treated is supplied from a source 405 of water to an inlet pressure relief valve 410. The inlet pressure relief valve 410 regulates inlet water pressure to prevent overpressurization and potential system damage. The inlet water then passes through a solenoid valve 415 and passes through a pre-filter 420. The pre-filter 420 removes particulate matter that may be present in the inlet water from the source 405. A first flow meter 425 monitors the flow of the inlet water from the pre-filter 420. An inlet water quality probe S1 is in fluid communication with inlet water exiting the pre-filter 420. The inlet water quality probe S1 includes a conductivity sensor and a temperature sensor. Conductivity of the inlet water may depend on both concentration of ionic species in the inlet water and temperature of the inlet water. The temperature sensor may provide data utilized to apply an offset or calibration to data output from the conductivity sensor to reduce or eliminate the effect of temperature on the conductivity sensor readings. In some embodiments, the raw conductivity readings from the inlet water conductivity sensor may be linearly adjusted for temperatures different from a reference temperature of 25° C. by a temperature coefficient, such as 2.0% per degree C.

The inlet water flows from the first flow meter 425 to a first treatment column 430 which may be, for example, a carbon filtration column. The water is treated in the first treatment column 430, exits the first treatment column 430, and enters a second treatment column 435 which may be, for example, a cation resin ion exchange column.

After being treated in the second treatment column 435 the water exits the second treatment column 435 and enters a third treatment column or worker bed 440. The worker bed 440 may include, for example, an anion resin ion exchange column. A worker probe S2 is disposed to measure at least one worker water parameter of water from the worker bed 440. The worker probe S2 may include a conductivity sensor and a temperature sensor for providing temperature calibration for data output from the conductivity sensor of the worker probe S2, as described above with reference to the inlet water quality probe S1. In some embodiments, the raw conductivity readings from the worker bed water conductivity sensor may be linearly adjusted for temperatures different from a reference temperature of 25° C. by a temperature coefficient, e.g., 5.2% per degree C. The temperature coefficient can be adjusted locally, at the unit or remotely, from the central server. The worker probe S2 may be provided on the output of the worker bed 440 to measure the quality of water exiting the worker bed 440. The worker probe S2 may include an indicator light or display (not shown) that provides an indication of whether the conductivity of the water exiting the worker bed 440 is within acceptable limits.

The water is treated in the worker bed and exits the worker bed 440 and enters a polisher bed 445 which may be, for example, a mixed bed resin ion exchange column. A polisher probe S3 is disposed to measure at least one polisher water parameter of water from the polisher bed 445. The polisher probe S3 may include a conductivity sensor and a temperature sensor for providing temperature calibration for data output from the conductivity sensor of the polisher probe S3, as described above with reference to the inlet water quality probe S1. In some embodiments, the raw conductivity readings from the polisher bed water conductivity sensor may be linearly adjusted for temperatures different from a reference temperature of 25° C. by temperature coefficient, e.g., 5.2% per degree C. The temperature coefficient can be adjusted locally, at the unit or remotely, from the central server. The polisher probe S3 may be provided on the output of the polisher column 445 to measure the quality of water exiting the polisher column

445. The polisher probe S3 may include an indicator light or display (not shown) that provides an indication of whether the conductivity of the water exiting the polisher column 445 is within acceptable limits. The water is treated in the polisher column 445 and exits the polisher column 445. The water exiting the polisher column 445 may pass through a post filter 450, which may be, for example, a column filter that filters any resin fines from the treated water. A second flow meter 425 may be provided downstream of the polisher bed 445. The second flow meter 425 may be provided in addition to or as an alternative to the first flow meter 425.

A monitor/controller 455, which may include features of one or both of the local monitor 225 and/or controller 110 illustrated in FIG. 2, may be utilized to monitor and control aspects of the system or unit 400. The monitor/controller 455 may, for example, receive a signal from a leak detector module 460 that may provide an indication of a leak being present in the system or unit 400. For, example, the leak detect module 460 may be disposed to close if moisture is detected in an enclosure 465 of the service deionization system 400 or on a floor or other surface upon which the enclosure 465 or the system 400 is disposed. The monitor/controller 455 may be configured to generate an indication, alarm, or warning if the leak detection module 460 detects moisture in the enclosure 465. If a leak is detected, the monitor/controller 455 may send a control signal to the solenoid valve to 415 to shut down flow of water through the system. The monitor/controller 455may also provide a signal by a wired or wireless connection to a service provider to indicate that the system 400 may be in need of service. The monitor/controller 455 may be configured to receive and monitor flow rate data via signals received from one or both of the first and second flow meters 425 and may be configured to receive and monitor at least one measured inlet water parameter from the inlet water quality probe S1, at least one worker water parameter from the worker probe S2, and at least one polisher water parameter from the polisher probe S3. The probes S1, S2, and/or S3 may provide conductivity measurements to the monitor/controller 455 at a periodic rate, for example, once every five seconds, or continuously. Data from the probes S1, S2, and/or S3 may be logged by the monitor/controller 455 on a periodic basis, for example, once per five minutes. If the flow rate or water quality measurements are outside an acceptable range the monitor/controller 455 may provide a signal by a wired or wireless connection to a service provider to indicate that the system 400 may be in need of service, for example, that the resin in one of the worker bed 440 or polisher bed 445 may be depleted and in need of replacement or that one of the filters 420, 450 may be clogged and in need of service.

Figure 5:
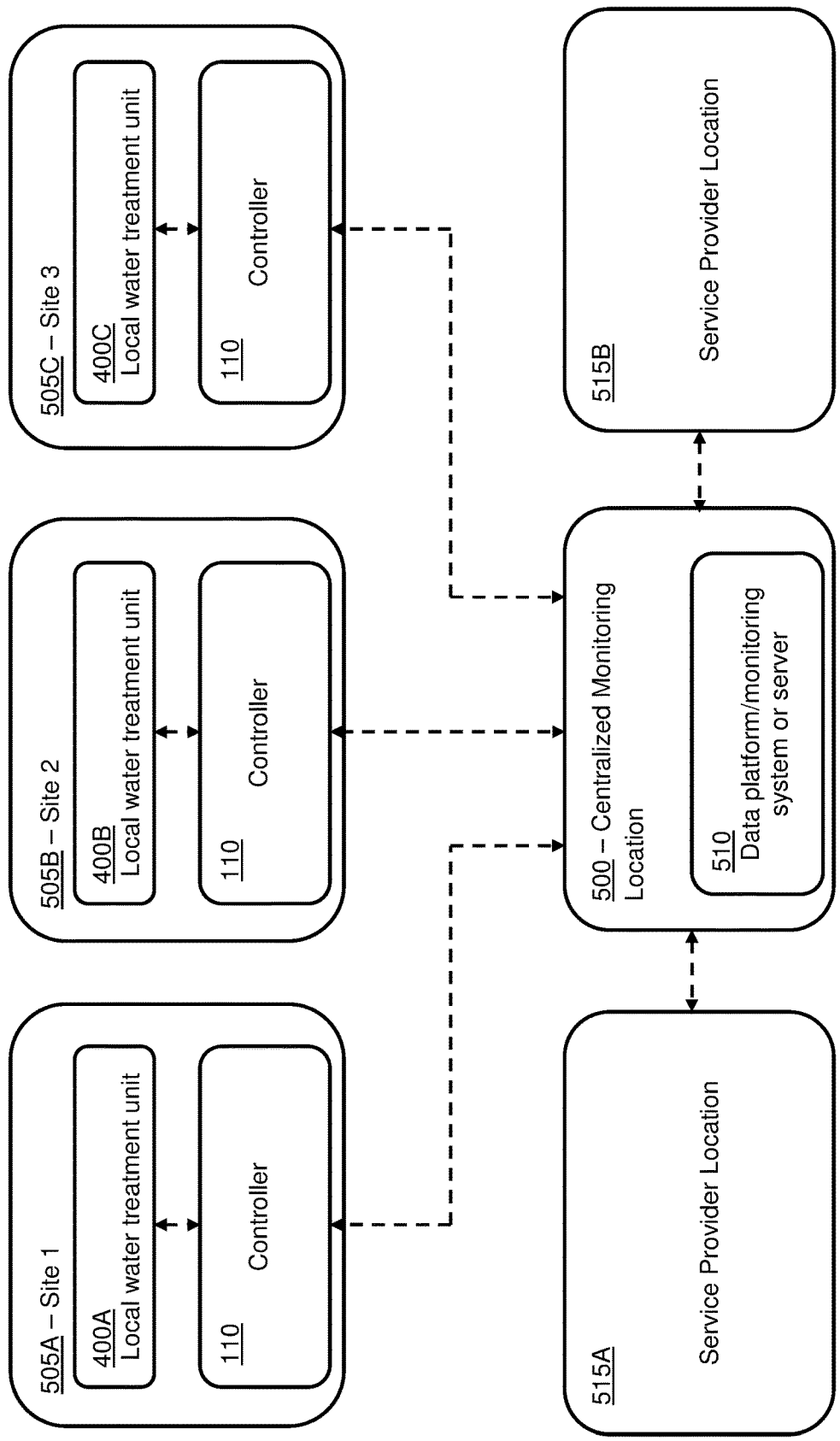
FIG. 5 is a schematic illustration of a water treatment system service.

The water treatment unit 400 (for example, the monitor/controller 455 of the water treatment system 400) may be in communication with a server, for example, server 510 at a centralized monitoring location 500 as illustrated in FIG. 5. The server 510 may be configured to receive from the local water treatment unit, at least one of the flow data, the at least one measured inlet water parameter, the at least one worker water parameter, and the at least one polisher water parameter.

At least one of the controller 455 and the server 510 may be further configured to determine at least one of a cumulative flow total based on an aggregate of the flow data from one or both of the first and second flow meters 425, a billing cycle flow total based on the flow data during a billing cycle through the local water treatment unit 400, a current exchange flow total based on the flow data during a current service period of the worker bed, a contaminant load based on the at least one inlet water parameter, and a remaining capacity of the local water treatment unit based at least on the contaminant load.

Additional sensors, for example, pressure differential sensors associated with the filters 420, 450, a flow sensor or flow totalizer associated with the inlet pressure relief valve 410 or first or second flow meters 425 may also be present and in communication with the monitor/controller 455, local monitor 225, and/or controller 110.

Certain aspects of the present disclosure are directed to a system and method for providing a service that allows delivery of a water product in accordance with specific quality requirements. In some instances, the product offering, e.g., the water product, is delivered and/or consumed by a user without the user operating any product treatment systems, e.g., without operating a water treatment system, and directly consumes the water product having predefined quality characteristics. In some instances, certain aspects of the disclosure allow acquisition of a user's consumption behaviour of the product, e.g., water consumption, and such data or information can then be utilized by the system owner or service product provider to adjust, repair, replace, or maintain, any component, subsystem, or parameter of, for example, the water treatment system. For example, one or more local treatment units or systems can be disposed or located at a user's facility with a plurality of ion exchange columns having a plurality of sensors or probes that monitor one or more characteristics thereof and/or one or more parameters of the raw, inlet water or feedwater, the outlet, service product water, and/or water exiting any of the ion exchange columns Data can thus be transmitted from the one or more treatment systems, e.g., at the users point of use, to an information or data storage or housing facility, typically away from the user's facility, or remotely from the water treatment system. Data or information acquired, transmitted and/or stored can include, for example, properties of the inlet water or the produced water quality, e.g., conductivity, pH, temperature, pressure, concentration of dissolved solids, oxidation reduction potential, or flow rate. Data acquired, transmitted, and/or stored can also include operating parameters of the one or more treatment systems. For example, the one or more treatment systems can deliver a deionized water product wherein the treatment system includes an ion exchange subsystem and the data can include any one or more of pressure, both inlet and outlet, flow rate, run-time, ion exchange bed operating or service duration, or alarm conditions. Other information can include subsystem characteristics such as remote transmitter signal strength, ion exchange bed pressure, and/or differential pressure.

With respect to an exemplary treatment system, the system can comprise ion exchange beds or columns of cation exchange resin, anion exchange resin, or a mixture of cation and anion exchange resin. The process can involve delivering water having a predetermined quality, e.g., a predetermined conductivity, for a predetermined period, e.g., hourly, daily, weekly, monthly, quarterly, semi-annually. For example, the process can provide a user with deionized water having a purity that is suitable for semiconductor manufacturing operations. The delivered water can be deionized at the user's facility by the one or more treatment systems even if the treatment system is not owned or operated by the user. The system's owner may provide the treatment system at the user's facility, connect the treatment system to a source of water, operate the treatment system, monitor the operating parameters of the treatment system, and deliver the treated, deionized water to the user. The system owner may receive information or data regarding the treatment system parameters and deionized water properties from the treatment system and store such data. The owner may monitor the system and proactively service or replace any subsystem or subcomponent of the treatment system without user interaction. The owner or operator of the treatment system thus provides a water product to the user without user interaction. For example, if data from the treatment system indicates that one or more of the ion exchange columns requires replacement, or is about to reach the end of its useful life, the owner or operator can, without user interaction, replace any of the columns of the treatment system. In exchange, the owner or operator is compensated by the user based on water consumption. Alternatively, the user can compensate the owner or operator according to a subscription, e.g., a daily, weekly, or monthly subscription for use and availability of the deionized water product.

Although a deionized product water treated by ion exchange columns was exemplarily described, other systems can be implemented as well. For example, the one or more treatment systems can utilize reverse osmosis (RO) apparatus. The owner or operator can remotely monitor the RO apparatus to ensure delivery and quality of a water product, replace RO membranes or columns, pumps, and/or filters, of the RO apparatus. In exchange, the user can compensate owner/operator based on quantity of produced water consumed, or according to a periodic subscription.

A centralized monitoring location, illustrated generally at 500 in FIG. 5 may receive data from one or more local water treatment systems, for example, from controllers 110 (and/or monitor/controllers 455, or local monitors 225) associated with local water treatment units or systems 400A, 400B, 400C at a plurality of different sites 505A, 505B, 505C. The local water treatment unit or system 400A located at one of the sites, for example, site 505A may be or may include the local water treatment unit or system 400 illustrated in FIG. 4. Another of the sites may include a second local water treatment unit or system 400B. The second local water treatment unit or system 400B may include unit operations similar to or corresponding to those of the local water treatment unit or system 400A, for example, a second inlet water quality probe (corresponding to inlet water quality probe S1 of treatment unit 400) disposed to measure at least one inlet water parameter of a second feedwater to be treated in the second local water treatment unit, the second inlet water quality probe including a second conductivity sensor and a second temperature sensor, a second worker bed (corresponding to worker bed 440 of treatment unit 400) having ion exchange media contained therein, and disposed to receive the second feedwater to be treated, a second worker probe (corresponding to worker probe S2 of treatment unit 400) disposed to measure at least one water parameter of water from the second worker bed, the second worker probe including a second worker conductivity sensor and a second worker temperature sensor, a second polisher bed (corresponding to polisher bed 445 of treatment unit 400) having ion exchange media contained therein, and fluidly connected downstream from the second worker bed, and a second polisher probe (corresponding to polisher probe S3 of treatment unit 400) disposed to measure at least one polisher water parameter of water from the second polisher bed, the second polisher probe including a second polisher conductivity sensor and a second polisher temperature sensor. A second flow meter (corresponding to first or second flow meter 425 of treatment unit 400) is positioned at least one of upstream the second worker bed and downstream of the second polisher bed and configured to measure flow data of water introduced into the second local water treatment unit. A second controller (corresponding to controller 455 of treatment unit 400) is in communication with the second flow meter, the second inlet water quality probe, the second worker probe, and the second polisher probe. The second controller is configured to receive the flow data from the second flow meter, the at least one measured inlet water parameter from the second inlet water quality probe, the at least one worker water parameter from the second worker probe, and the at least one polisher water parameter from the second polisher probe.

The second water treatment system 400B, like the water treatment system 400, may be in communication with the server 510 at the centralized monitoring location 500. The server 510 may be further configured to receive from the second local water treatment unit, at least one of the flow data from the second flow meter, the at least one measured inlet water parameter from the second inlet water quality probe, the at least one worker water parameter from the second worker probe, and the at least one polisher water parameter from the second polisher probe.

At least one of the controller 455 of local water treatment system 400 and the server 510 may be further configured to determine at least one of a cumulative flow total based on an aggregate of the flow data from one or both of the first and second flow meters 425, a billing cycle flow total based on the flow data during a billing cycle through the local water treatment unit 400, a current exchange flow total based on the flow data during a current service period of the worker bed, a contaminant load based on the at least one inlet water parameter, and a remaining capacity of the local water treatment unit based at least on the contaminant load.

A second controller at the second water treatment unit 400B, which may be substantially similar to and correspond to the controller 455 of local water treatment system 400 may be configured to determine at least one of a cumulative flow total of the second water treatment unit based on an aggregate of the flow data through the water second water treatment unit, a second billing cycle flow total based on the flow data during a billing cycle through the second water treatment unit, a current exchange flow total based on the flow data during a current service period of the second worker bed, a second contaminant load based on the at least one inlet water parameter of the second feedwater, and a remaining capacity of the second local water treatment unit based at least on the second contaminant load.

Data from any of the units 400A, 400B, and 400C can be collected and respectively stored in a memory device operatively connected to each of the respective controllers 110 and continuously transmitted through wired or wireless communication protocols or a combination thereof to server 510. Typically, however, data at each unit is stored and accumulated during a predetermined collection period and then transmitted intermittently to server 510. For example, data regarding the various operating parameters can be continually or continuously collected and stored the memory device, the controller can periodically, e.g., every five minutes, hourly, once or twice each day, transmit through the modem to a receiving modem operatively connected via an internet connection to server 510 whereat the accumulated data can be stored and analyzed. In other configurations, certain data types, such as alarms and associated notifications, may be preferentially transmitted immediately.

The centralized monitoring location 500 may analyze the data provided by the different controllers 110 to determine when one or more water treatment devices 105 in the water treatment systems at the different sites 505A, 505B, 505C should be serviced. The centralized monitoring location 500 may create a schedule for service of the one or more water treatment devices 105 in the water treatment systems at the different sites 505A, 505B, 505C and communicate service schedules to one or more service provider locations 515A, 515B.

In some embodiments a service provider responsible for servicing components of a water treatment system at a user's site may obtain data from the water treatment system and charge a fee for providing treated water at the user's site based on the data obtained from the water treatment system. The fee may include a base monthly charge for an expected amount of treated water to be produced and a surcharge for a measured amount of treated water produced over the expected amount. In some embodiments, a water treatment system or component thereof, for example, one or more of the ion exchange columns 430, 435, 440, 445 illustrated in FIG. 4 may have a finite capacity for treating water having a certain impurity concentration before the water treatment system or component thereof becomes depleted or should be serviced. An ion exchange column, for example, may have a capacity for removing a certain amount of undesirable ions from water passing through the ion exchange column before resin in the ion exchange column may need to be regenerated or replaced.

A service provider, who, in some implementations may also be the owner of a water treatment system providing treated water at a user's site, may monitor parameters of influent water to be treated, for example, flow rate and water quality. These parameters may be collected by a controller 110 and/or monitor/controllers 455, or local monitors 225 as described above and communicated to a central server 510 or service hub at a centralized monitoring system 500 as illustrated in FIG. 5. The service provider may charge a fee for producing the treated water for the user that is based at least in part on the parameters of the influent water to be treated, for example, flow rate and water quality. The fee for providing treated water over a predetermined time period, for example, over a week, a month, or a year, may be based on an average flow rate and average water quality over the predetermined time period. In calculating the average flow rate and/or average water quality over the predetermined time period outliers in the flow rate or water quality data may be removed to provide a better indication of steady state operation of the water treatment system.

Figure 4:
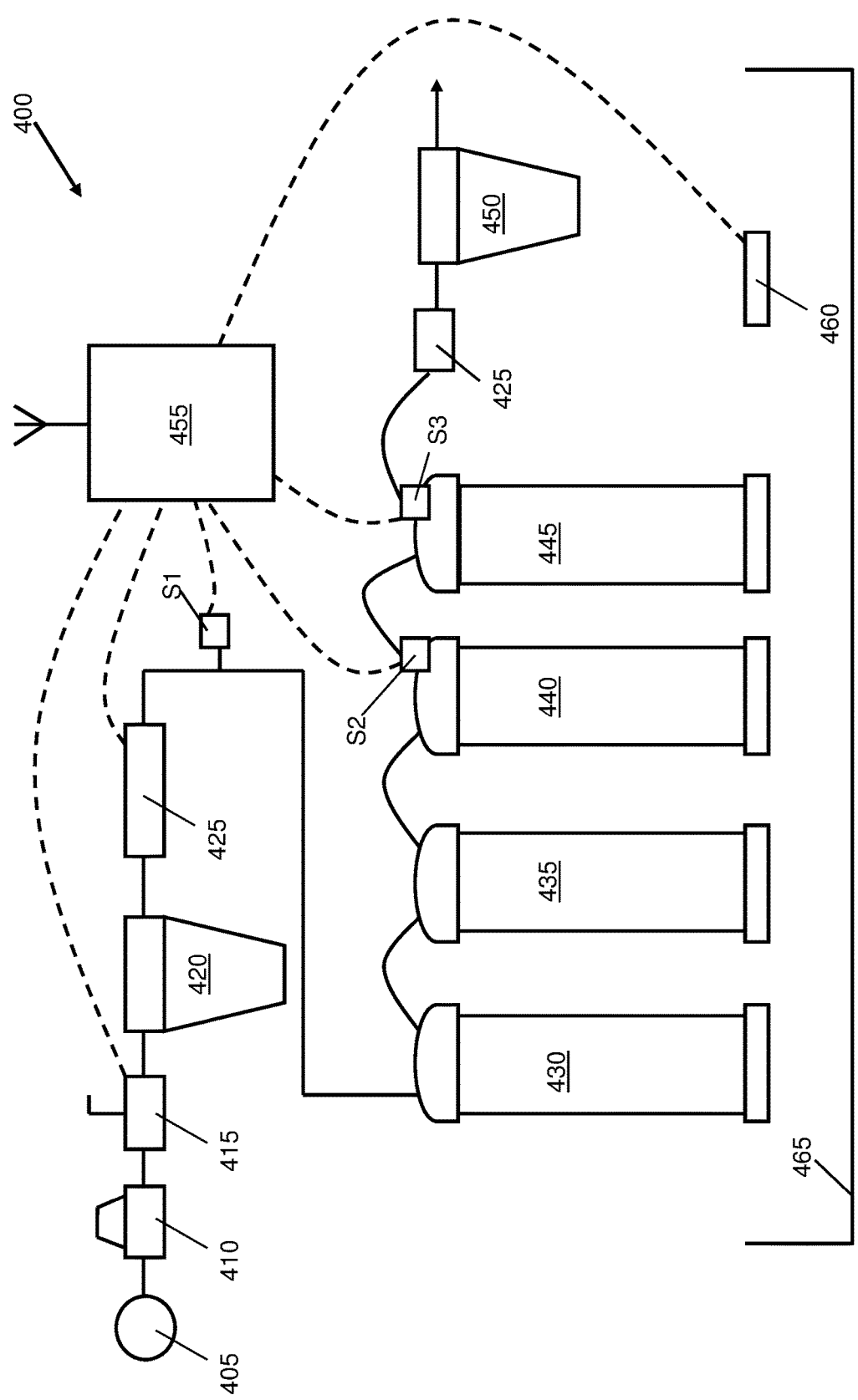
FIG. 4 is a schematic illustration of a service deionization water treatment system.

A service deionization system such as illustrated in FIG. 4 is one example of a water treatment system or unit at a user's site that a service provider may maintain and service and charge the user for treating influent water to produce treated water at the user's site. Resin beds in the ion exchange columns 430, 435, 440, 445 may have a limited capacity for removing ionic contaminants from water undergoing treatment at the user's site. The ion exchange columns may be periodically serviced by the service provider to, for example, replace ion exchange media in the ion exchange columns. A fee that the service provider charges for the provision of the treated water at the user's site may be based at least partially on costs associated with replacing the ion exchange media in the ion exchange columns and the frequency at which such service is performed.

The time between instances of service to replace ion exchange media in an ion exchange column may be calculated based on a water quality parameter such as concentration of ionic contaminants in influent water to be treated and a flow rate of water through the water treatment system. A conductivity sensor (e.g., one of the input sensors 205 illustrated in FIG. 2) may be utilized to measure the concentration of ionic contaminants in the influent water to be treated. A flow sensor (e.g., another of the input sensor 205 illustrated in FIG. 2 or the output sensors 215 or internal sensors 210 illustrated in FIG. 2) may be utilized to measure the flow rate of water being treated in the water treatment system at the user's site. Based on measurements from the conductivity sensor and the flow sensor(s) in the water treatment system, the service provider may determine a frequency at which the ion exchange column(s) should be serviced. The capacity of the ion exchange columns is based on the types of resin used and the amount of resin used. The capacity is expressed in grains. The total amount of water that can be treated is based on the capacity of the ion exchange columns and contaminant load in the feedwater as expressed by its conductivity. The conversion equations are as follows:

$$\text{Conductivity (uS/CM)} \times \text{Cond\_TDS\_Conv\_Factor} = \text{Total Dissolved Solids (TDS) (units are PPM)} \quad (1)$$

$$\text{TDS/PPM\_GPG\_Conv\_Factor} = \text{Contaminant\_Load (units are grains/gallon)} \quad (2)$$

The Cond_TDS_Conv_Factor and PPM_GPG_Conv_Factor factors in the above equations may be empirically determined.

Capacity calculations may begin (or may be reset) when the ion exchange columns are exchanged. When water begins flowing through the ion exchange columns the feedwater conductivity is converted to Contaminant_Load per equatons (1) and (2) above. Each gallon of water that flows reduces the ion exchange column capacity by gallons flowed×Contaminant_Load. At the beginning of each day, the system computes the projected days left until ion exchange column exhaustion (Projected Days Left) by using the previous days average conductivity, the 10 day average flow total and current remaining capacity per the following equation:

$$(\text{Current Remaining Capacity}/(\text{Average Daily Conductivity} * \text{Cond\_TDS\_Conv\_Factor/PPM\_GPG\_Conv\_Factor}))/10 \text{ Day Average Flow Total} = \text{Projected Days Left} \quad (3)$$

The projected days left is compared to a projected days alarm setpoint. If it is less than the setpoint and a projected days left alarm is generated.

If the percent of remaining capacity is less than a remaining capacity alarm setpoint, a remaining capacity alarm is generated.

Alternatively, capacity determination may be based on a historically weighted calculation of average flow rate weighted relative to the past day flow rate. For example, a historical daily average flow rate and the prior day average flow rate can be weighted, e.g., 1:1, 2:1, 3:1, 4:1, 5:1, 6:1, 7:1, 3:2, 4:3, 5:2, 5:3, 6:5, 7:2, 7:3, 7:4, 7:5, and 7:6, can be used.

The service provider may schedule servicing of the ion exchange column(s) so that the ion exchange column(s) are serviced while still having a certain amount of treatment capacity, for example, 10% treatment capacity remaining (a remaining capacity alarm setpoint of 10%) to provide a safety margin to prevent the treated water from achieving an unacceptable quality. The service provider may also or alternatively schedule servicing of the ion exchange column(s) at a set period of time, for example, from five to ten days before the treatment capacity of the ion exchange column(s) is expected to become depleted. The service provider may set a fee for production of specified volume of treated water at the user's site based on the calculated frequency at which the ion exchange column(s) should be serviced.

The service provider may also or alternatively schedule service of the water treatment system based on alarms or out of control signals provided by the water treatment system. The alarms or out of control signals may be sent responsive to one or more monitored parameter exceeding a setpoint or being outside of an expected range (e.g., 5% or more above a five day average or a 10 day average) at a single point in time or for a period of time, for example, for five days or more. For example, for a service deionization system such as illustrated in FIG. 4, worker probe S2 may provide an indication that the conductivity of water exiting the ion exchange column 440 is increasing to a level indicative of imminent depletion of the ion exchange bed in the ion exchange column 440. The service provider may receive a notification of the indication from worker probe S2 via, for example, the monitor/controller 455 and may schedule service of the ion exchange column 440. Based on the conductivity readings from the worker probe S2 and the measured flow rate through the system, the service provider may calculate a remaining treatment capacity of the ion exchange bed in the ion exchange column 445 and adjust a schedule for servicing the ion exchange column 445 accordingly. In some embodiments, the ion exchange column 440 should be serviced within about two days from the indication provided from the sensor S1. Additionally, if the polisher probe S3 provides an indication that the conductivity of the water exiting the ion exchange column 445 is approaching or exceeding an unacceptable level, if the leak sensor 460 provides an indication of a water leak, or if a pressure sensor or sensors (e.g., one or more of sensors 205, 210, or 215 of FIG. 2) provides an indication of an unacceptable or unacceptably trending pressure across one or more components of the treatment system, the service provider may schedule a service call to service one or more of the components of the water treatment system.

The service provider may also or alternatively schedule service based on one or more signals indicative of a potential system problem from one of the ancillary systems 150A, 150B, 150C illustrated in FIG. 1B, for example, failure of a pump, unexpectedly high power draw from one of the ancillary systems, unacceptable pressure drop across one of the ancillary systems, etc. Any alerts, alarms, or out of control signals provided to the service provider may also or alternatively be provided to a user of the treated water produced by the water treatment system, an operator of the water treatment system or a component thereof, or an owner of the system or component thereof if the owner is not the service provider.

In some embodiments, the central server 510 located at the centralized monitoring location 500 may determine when and which components of water treatment systems at various user or customer sites 505A, 505B, 505C should be serviced. The central server located at the centralized monitoring location 500 may communicate a service schedule to one or more service provider locations 515A, 515B. The central server 510 located at the centralized monitoring location 500 may send service requests or schedules to one or one or more service provider locations 515A, 515B that optimize factors such as travel time between the service provider locations 515A, 515B and sites at which equipment may be in need of service. For example, the central server may send a service schedule to a service provider location that is closer to a site having equipment that should be serviced than another service provider location. The central server may adjust the service schedule so that one or more components of a water treatment system at one of user or customer sites 505A, 505B, 505C is serviced earlier or later than optimal based on the remaining treatment capacity of the one or more components if doing so would provide for multiple components to be serviced in a single service trip and thus cause an overall reduction in costs by reducing a number of individual service trips that are taken by the service provider. For example, if service is scheduled to replace an ion exchange column (or columns) at a first site, and a second site close to the first site has one or more ion exchange columns that have a remaining capacity of less than about 10% more than their remaining capacity alarm setpoint and/or a Projected Days Left of a week or less, replacement of the ion exchange column(s) at the second site may be scheduled to be performed during a same service trip to replace the ion exchange column(s) at the first site.

Costs associated with regenerating ion exchange columns may also be factored into decisions on when to replace ion exchange columns approaching exhaustion at different sites. With some ion exchange columns if the resin in the ion exchange column still has remaining treatment capacity, the resin bed may be first completely exhausted prior to being regenerated. To exhaust the resin bed, additional chemicals may be passed through the resin bed. More chemicals may be required to exhaust and then regenerate an ion exchange column with 20% remaining capacity than a similar ion exchange column with 10% remaining capacity. The chemicals used to exhaust a resin bed in an ion exchange column have an associated cost. Accordingly, if, in the example above, costs (e.g., fuel costs and worker time) associated with travel to the second site in addition to costs associated with the chemicals used for regenerating the ion exchange columns at the second site earlier than necessary exceed costs (e.g., fuel, labor, etc.) that might be associated with replacing the ion exchange columns at the second site in a different service trip than the service trip for replacing the ion exchange column(s) at the first site, different service trips for the two different sites may be scheduled instead of just one.

Components of a water treatment system which may be serviced by a service provider are not limited to ion exchange columns and the water quality parameter or parameters used to determine when to service the components water treatment systems are not limited to conductivity or ionic concentration and flow rate. In other embodiments, a water treatment system may include a turbidity sensor upstream of one or more water treatment devices. The one or more water treatment devices may have a limited capacity for removing turbidity from water undergoing treatment in the one or more water treatment devices. The one or more water treatment devices may include, for example, a filter (e.g., a sand filter or other form of solids-liquid separation filter) that has a limited capacity for removal of solids from water before becoming clogged or otherwise rendered ineffective for further treatment of turbidity. The flow rate of water through the one or more water treatment devices and the turbidity of the water to be treated may be monitored to determine an expected service lifetime of the one or more water treatment devices. Service of the one or more water treatment devices may then be scheduled to be performed prior to the end of the service lifetime of the one or more water treatment devices.

In another example, the one or more water treatment devices may include a pressure-driven separation device, for example, a nanofiltration device or a reverse osmosis device and the parameters used to determine when the one or more water treatment devices should be serviced include pH and/or temperature measured by one or more pH or temperature sensors upstream, downstream, or within the one or more water treatment devices.

Figure 6:
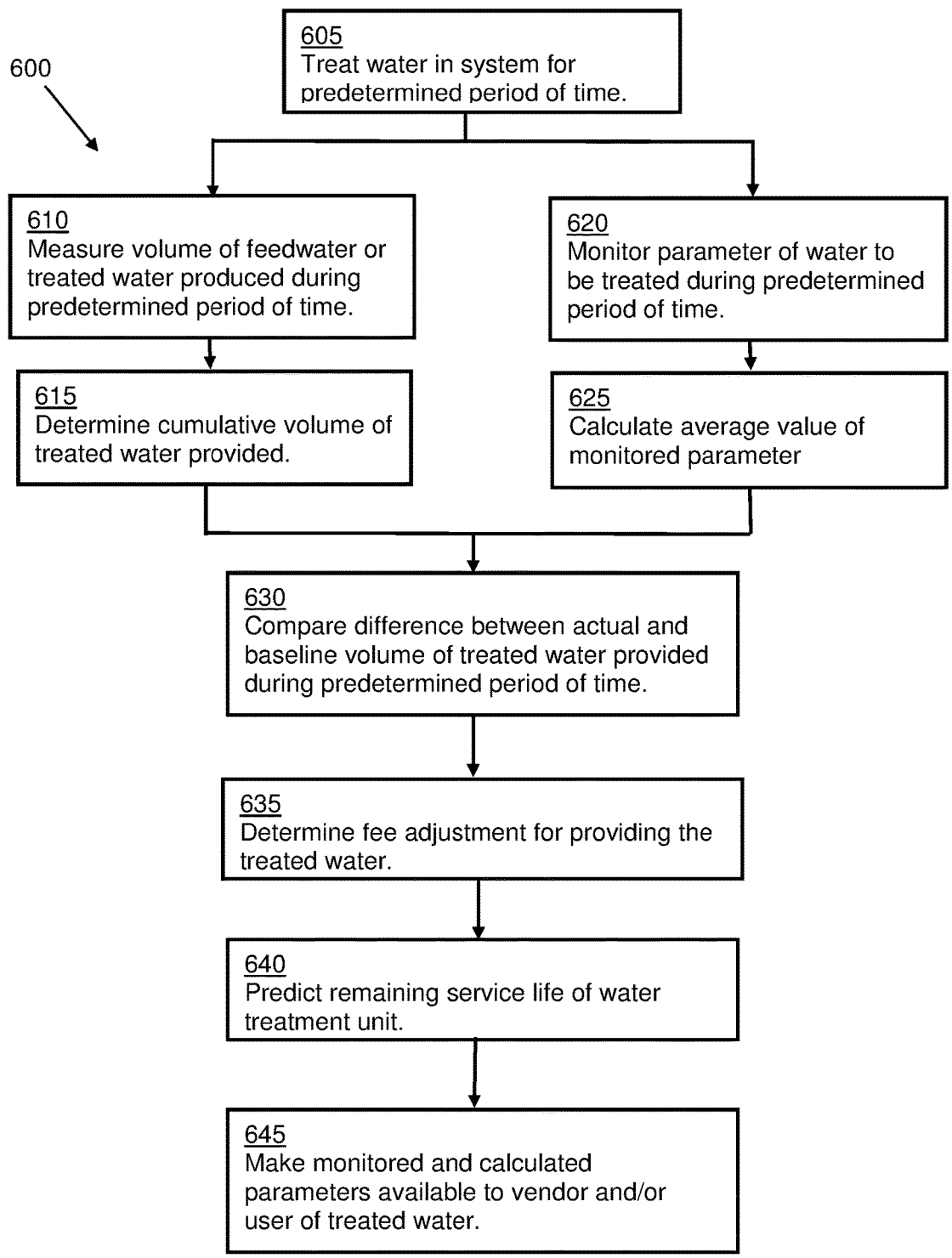
FIG. 6 is a flowchart of a method of providing treated water.

One method of providing treated water utilizing embodiments of the system disclosed herein is illustrated in the flowchart of FIG. 6, indicated generally at 600. In act 605 of the method, water is treated in a water treatment unit, for example, that described with reference to any of FIGS. 1A, 1B, 2, and 4, for a predetermined period of time to produce treated water. The predetermined period of time may correspond to a billing cycle of a vendor or service provider who services the water treatment unit, operates the water treatment unit on behalf of a customer, or who owns the water treatment unit. The predetermined period of time may be, for example, a week, a month, three months, or any other suitable period of time. During the predetermined period of time, a volume of the water or feedwater to be treated and/or the treated water provided by the water treatment unit is measured utilizing a sensor positioned in the water treatment unit, for example, one of the ancillary devices 105A, 105B, 105C of FIG. 1B, the input or output sensors 205, 215 of FIG. 2, or one or both of the flow meters 425 of FIG. 4. (Act 610.) In some embodiments, after measuring the volume of the treated water provided by the water treatment unit in act 610, a cumulative volume of treated water provided by the water treatment unit may be determined (act 615). During the predetermined period of time, one or more parameters of water to be treated in the water treatment system is monitored utilizing a water quality sensor positioned in the water treatment unit, for example, using the ancillary device 105A of FIG. 1B or one of the input sensors 205 of FIG. 2. (Act 615.) Monitoring the one or more parameters of the water to be treated may comprise monitoring a conductivity of the water to be treated. The average of the value of the one or more parameters of the water to be treated during the predetermined period of time may be calculated in act 625.

The method further includes calculating a difference between the measured volume of the provided treated water during the predetermined period of time and a baseline volume of treated water to be provided during the predetermined period of time (act 630) and determining a fee adjustment for providing the treated water based at least on the calculated difference between the measured volume of the provided treated water and the baseline volume of treated water to be provided (act 635). The fee adjustment may also be based on the monitored parameter, the average of the value of the monitored parameter during the predetermined period of time, and/or a difference between the monitored parameter and an expected value of the monitored parameter. The fee adjustment may be an adjustment to a base fee for providing the treated water during the predetermined period of time that is determined based on at least one of an expected volume of the feedwater to be treated during the predetermined period of time and an expected value of the parameter of the water to be treated during the predetermined period of time.

In act 640, a remaining service life of the water treatment unit may be predicted based on at least one of the measured volume of the treated water provided and/or a cumulative volume of the feedwater directed through the water treatment unit during the predetermined period of time and the monitored parameter. In some embodiments, the monitored parameter relates to a conductivity of the water to be treated. The remaining service life of the water treatment unit may be determined based at least on the cumulative volume of treated water and on the monitored parameter or an average of the value of the monitored parameter during the predetermined period of time and/or a treatment capacity of the water treatment unit.

In act 645 data regarding any of the monitored or calculated parameters, for example data indicative of one or more of: cumulative volume of water to be treated during the predetermined period of time, expected volume of water to be treated during the predetermined period of time, volume of treated water provided during the predetermined period of time, measured parameter of the water to be treated during the predetermined period of time, and expected value of the parameter of the water to be treated during the predetermined period of time may be made available to a user of the water to be treated (a customer) or a vendor or service provider responsible for operating or servicing the water treatment system. This data may be made available, for example, via a web portal (e.g., web portal 120 of FIG. 1A) and/or transmitted to a central server remote from the water treatment system (e.g., server 510 of FIG. 5). In some embodiments, a schedule for service of the water treatment system may be determined without input from a user of the treated water, for example, based on the data provided to the central server.

The method of FIG. 6 may be performed for any number of water treatment units, for example, a first water treatment unit located at site 1, illustrated in FIG. 5 and a second water treatment unit located at site 2 illustrated in FIG. 5, remote from the first water treatment unit.

Figure 7:
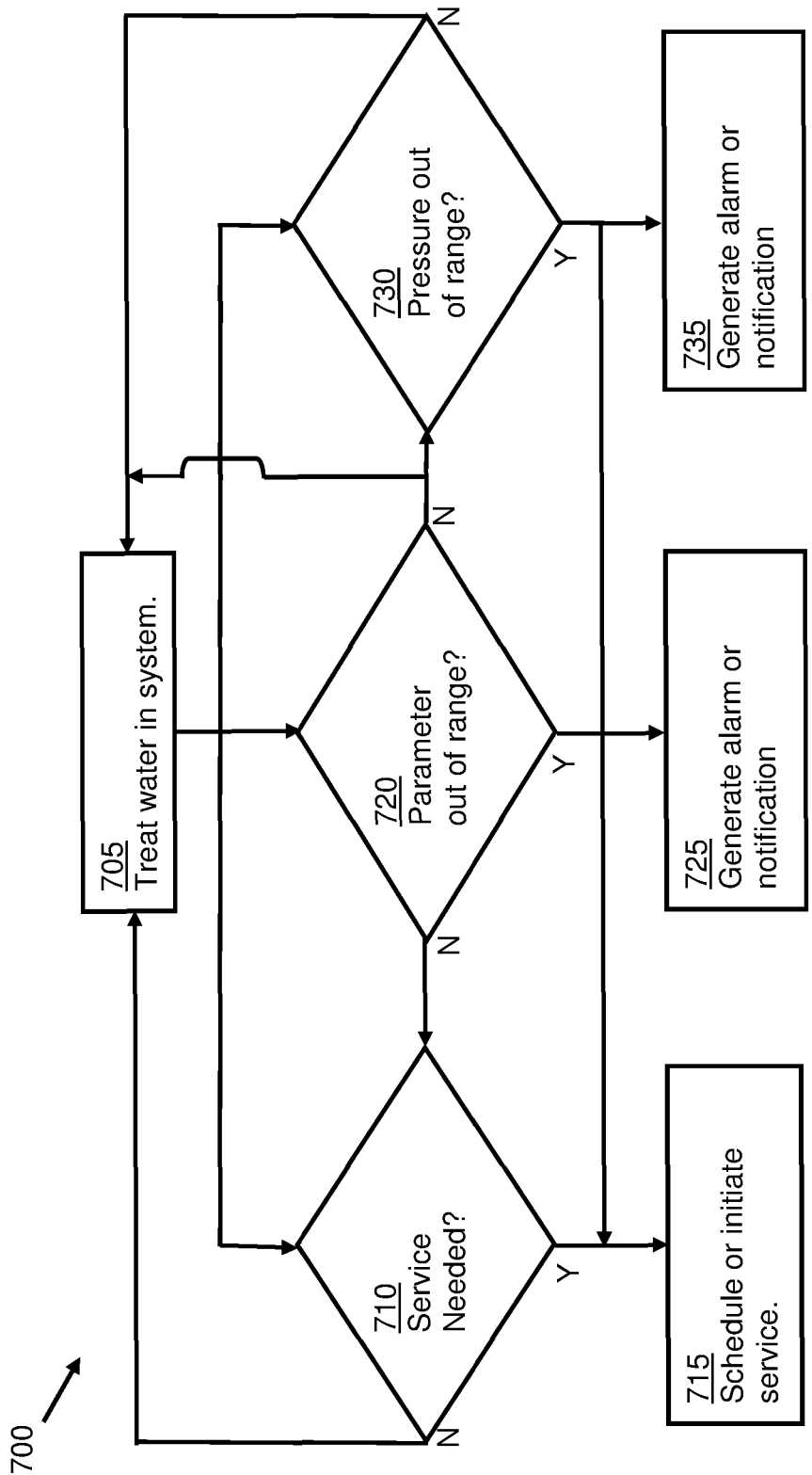
FIG. 7 is a flowchart of a method of performing actions based on data collected by a water treatment unit during treatment of water.

FIG. 7 illustrates various actions that may be performed responsive to data gathered or calculated in the method of FIG. 6. In the flowchart indicated generally at 700, in act 705, the water treatment system is treating water. During treatment of the water, the water treatment system, or associated monitor(s) or controller (local or remote) may check the status of various parameters or conditions of the water treatment system. Any one or more of these various parameters or conditions may be checked continuously, on a predetermined schedule, sequentially, or concurrently. One condition that may be checked is whether the system is in need of or will soon be in need of service (act 710). To determine if the system is in need of service, a remaining service life of the system, determined, for example, in act 640 of the method illustrated in FIG. 6, is compared against a service-initiating life of the water treatment unit. If the remaining service life is less than a service-initiating life of the water treatment unit, service of the water treatment unit may be scheduled (act 715). The water treatment system or associated monitor(s) or controller may also check whether a monitored parameter of the treated water provided by the system, for example, conductivity, particle level, ORP, or any of the other parameters described with reference to the ancillary devices of FIG. 1B or output sensor(s) of FIG. 2 is outside of a desired range (act 720). If the monitored parameter is outside of the desired range, the system or associated monitor(s) or controller may at least one of: generate an alarm, send a notification to a user, or schedule service of the water treatment unit (acts 715, 725). If the monitored parameter is within the desired range the water treatment unit may continue treating water, optionally after performing checks of one or more additional conditions. Another parameter that may be checked or monitored by the system or associated monitor(s) or controller may be pressure across the water treatment unit (act 730). If the monitored pressure exceeds a predetermined differential pressure unit, the system or associated monitor(s) or controller may at least one of: generate an alarm, send a notification to a user, or schedule or initiate service of the water treatment unit (acts 735, 725). If the pressure across the water treatment unit is within an acceptable range, the water treatment unit may continue treating water, optionally after performing checks of one or more additional conditions. Notification may be any one or more of a text message, e.g., SMS or MMS, email message, a haptic alarm, an audible alarm, and a visual alarm.

Figure 8:
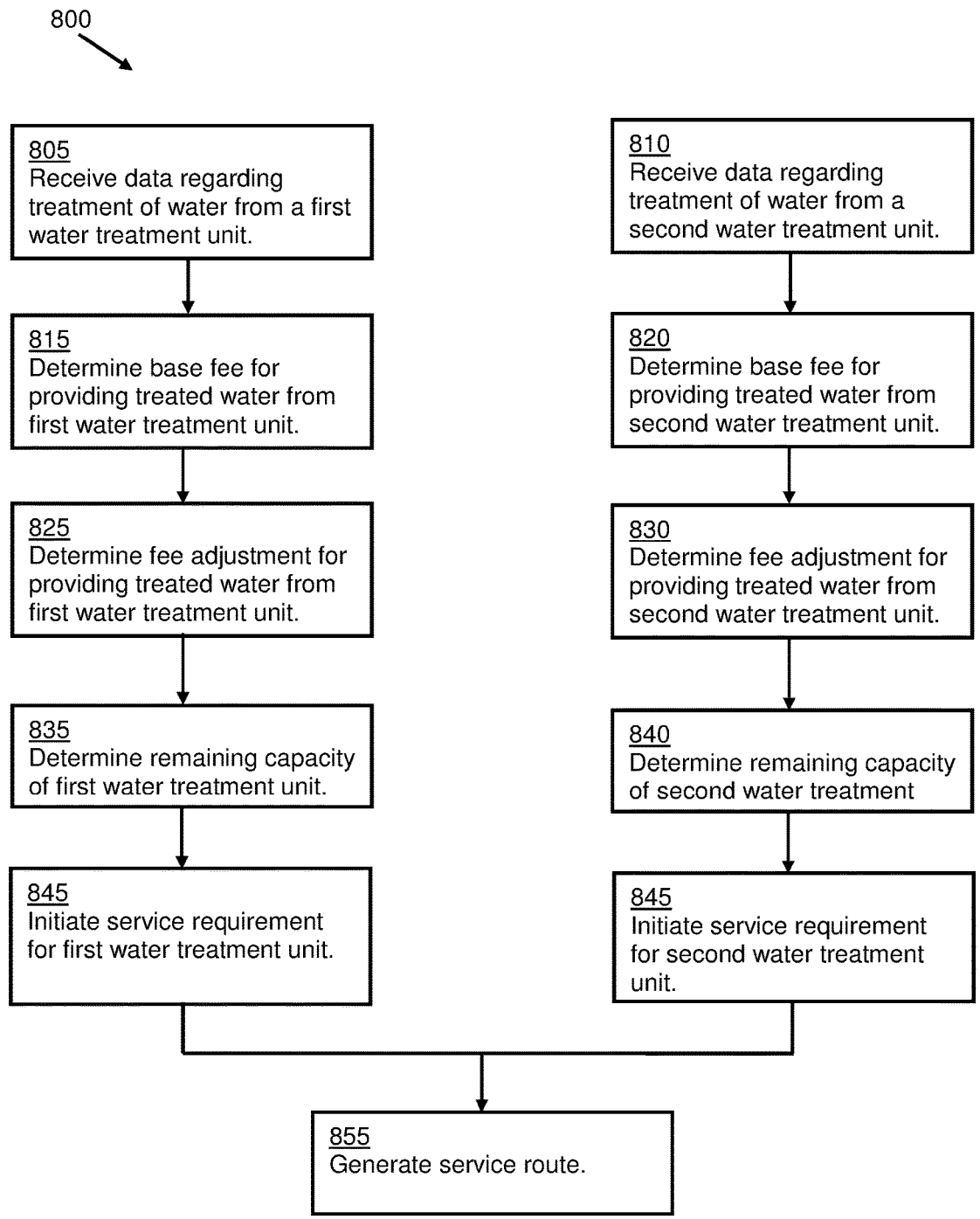
FIG. 8 is a flowchart of a method of remotely monitoring water treatment units.

A method of remotely monitoring water treatment units is illustrated in the flowchart of FIG. 8, indicated generally at 800. Act 805 involves receiving at a central server, for example, server 510 of FIG. 5, data from a first water treatment unit that produces a first treated water delivered to a first facility the central server is disposed remotely from. The data may be representative of at least one of a volume of a first feedwater to be treated in the first water treatment unit, a volume of the first treated water, and a conductivity of the first feedwater, during a first predetermined period.

Act 810, which may be performed concurrently or sequentially with act 805, involves receiving at the central server, data from a second water treatment unit that produces a second treated water delivered to a second facility that is disposed remotely from the first facility and that the central server is disposed remotely from. The data may be representative of at least one of a volume of a second feedwater to be treated in the second water treatment unit, a volume of the second treated water, and a conductivity of the second feedwater, during a second predetermined period.

In act 815, a first base fee for providing the first treated water over the first predetermined period is determined based on at least one of an expected volume of the first feedwater to be treated and an expected value of the conductivity of the first feedwater.

In act 820, a second base fee for providing the second treated water over the second predetermined period is determined based on at least one of an expected volume of the second feedwater to be treated and an expected value of the conductivity of the second feedwater.

In act 825, a first fee adjustment for providing the first treated water is determined based on the first base fee and a difference between an actual and the expected volume of the first feedwater. The first fee adjustment may further be based on the conductivity of the first feedwater during the first predetermined period.

In act 830, second fee adjustment for providing the second treated water is determined based on the second base fee and a difference between an actual and the expected volume of the second feedwater. The second fee adjustment may be further based on the conductivity of the second feedwater during the second predetermined period.

In act 835, a remaining treatment capacity of the first water treatment unit is determined based at least on at least one of a cumulative volume of the first feedwater and the conductivity of the first feedwater directed through the first water treatment unit.

In act 840, a remaining treatment capacity of the second water treatment unit based at least on at least one of a cumulative volume of the second feedwater and the conductivity of the second feedwater directed through the second water treatment unit.

In act 845, a first service requirement for the first water treatment unit is initiated based on a cumulative volume of the first feedwater treated in the first treatment unit.

In act 850, a second service requirement for the second water treatment unit is initiated based on a cumulative volume of the second feedwater treated in the second treatment unit.

In act 855, a route for a service provider to service the first water treatment unit and the second water treatment unit is generated based at least in part on locations of each of the first facility and the second facility.

EXAMPLE

Fee adjustments applied to an invoice to a consumer of treated water may be determined in proportion to the amount of treated water above or below the volume that was expected to be provided during a billing period, or may be adjusted in a tiered fashion based on the difference between actual and expected volume of treated water provided during the billing period.

In an example of a proportional fee adjustment schedule, if a consumer of treated water was expected to use X gallons of treated water during a billing period, the consumer may receive a fee adjustment credit that may be applied to an invoice for the billing period or subsequent billing period for each gallon less than the expected volume that was provided during the billing period. The consumer may receive a fee adjustment charge that may be applied to an invoice for the billing period or subsequent billing period for each gallon more than the expected volume that was provided during the billing period. The amount of the credit provided per gallon below the expected volume provided need not be the same as the charge per gallon above the expected volume provided, although it may be. In some embodiments, consumers of treated water may receive a fee adjustment charge for excess treated water production, but may not be entitled to a fee adjustment credit for consuming less than the expected volume of treated water.

In an example of a tiered fee adjustment schedule, if a consumer of treated water was expected to use X gallons of treated water during a billing period, the consumer may receive a fee adjustment credit that may be applied to an invoice for the billing period or subsequent billing period if the consumer consumed at least Y gallons less (a first tier) than the expected volume during the billing period. If the consumer consumed less than the expected volume but no more than Y gallons less, the consumer would not be entitled to the credit. An additional credit may be provided to the consumer if the consumer consumed at least Z gallons less (a second tier) than the expected volume during the billing period, Z>Y. In some embodiments Z may equal 2*Y. Additional credits may be provided for additional tiers of water consumption below the expected volume. The volume of water corresponding to intervals between each sequential tier may correspond to the same volume of water (e.g., Z=2*Y), although the intervals between sequential tiers may correspond to greater or lesser volumes of water. The amount of credit for consuming less water in different sequential tiers may be a multiple of the credit for consuming less water than that associated with the first tier. For example, the consumer may receive a credit of $A for consuming a sufficiently low volume of water to reach the first credit tier and $2*A for consuming a sufficiently low volume of water to reach the second credit tier (and $3**A for reaching third credit tier, etc.). In other embodiments, the consumer may receive greater or less than a multiple of the credit for consuming less water than that associated with the first tier for consuming a sufficiently low volume of water to reach the second credit tier or further sequential credit tiers.

The consumer may receive a fee adjustment charge that may be applied to an invoice for the billing period or subsequent billing period if the consumer consumed at least N gallons more (a first tier) than the expected volume during the billing period. If the consumer consumed more than the expected volume but less than N gallons more, the consumer would not be charged the fee adjustment charge. An additional charge may be applied to the consumer's invoice if the consumer consumed at least M gallons more (a second tier) than the expected volume during the billing period, M>N. In some embodiments M may equal 2*N. Additional charges may be applied for additional tiers of water consumption above the expected volume. The volume of water corresponding to intervals between each sequential tier may correspond to the same volume of water (e.g., M=2*N), although the intervals between sequential tiers may correspond to greater or lesser volumes of water. The charge for consuming more water in different sequential tiers may be a multiple of the charge for consuming more water than that associated with the first tier. For example, the consumer may receive a charge of B for consuming a sufficiently large volume of water to reach the first fee adjustment charge tier and $2*B for consuming a sufficiently large volume of water to reach the second fee adjustment charge tier (and $3*B for reaching the third fee adjustment charge tier, etc.). In other embodiments, the consumer may be charged greater or less than a multiple of the charge for consuming more water than that associated with the first tier for consuming a sufficiently large volume of water to reach the second fee adjustment charge tier or further sequential fee adjustment charge tiers.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. For example, although aspects of the present disclosure are described as used to remove biological floc from wastewater, these aspects may be equally applicable to the removal of any form of suspended solids, for example, inorganic suspended solids or fats, oil, or grease in a settling unit or vessel. Aspects of the wastewater treatment systems described herein may also use non-biological treatment methods rather than biological treatment methods for the treatment of wastewater. Accordingly, the foregoing description and drawings are by way of example only.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A system for providing treated water, the system comprising:
   a local water treatment unit including:
      an inlet water quality probe disposed to measure at least one inlet water parameter of feedwater to be treated, the inlet water quality probe including a conductivity sensor and a temperature sensor,
      a worker bed having ion exchange media contained therein, and disposed to receive the feedwater to be treated,
      a worker probe disposed to measure at least one worker water parameter of water from the worker bed, the worker probe including a worker conductivity sensor and a worker temperature sensor,
      a polisher bed having ion exchange media contained therein, and fluidly connected downstream from the worker bed,
      a polisher probe disposed to measure at least one polisher water parameter of water from the polisher bed, the polisher probe including a polisher conductivity sensor and a polisher temperature sensor,
      a flow meter positioned at least one of upstream of the worker bed and downstream of the polisher bed and configured to measure flow data of water introduced into the local water treatment unit,
      a controller in communication with the flow meter, the inlet water quality probe, the worker probe, and the polisher probe, the controller configured to receive the flow data from the flow meter, the at least one measured inlet water parameter from the inlet water quality probe, the at least one worker water parameter from the worker probe, and the at least one polisher water parameter from the polisher probe; and
   a server remote from and in communication with the local water treatment unit, the server configured to receive from the local water treatment unit, at least one of the flow data, the at least one measured inlet water parameter, the at least one worker water parameter, and the at least one polisher water parameter, at least one of the controller and the server further configured to:
      determine a billing cycle flow total based on the flow data during a billing cycle through the local water treatment unit
      calculate a difference between the billing cycle flow total and a baseline volume of treated water expected to be provided during the billing cycle; and
      determine a fee adjustment for providing the treated water based on the calculated difference between the billing cycle flow total and the baseline volume of treated water expected to be provided.

2. The system of claim 1, further comprising:
   a second local water treatment unit including
   a second inlet water quality probe disposed to measure at least one inlet water parameter of a second feedwater to be treated in the second local water treatment unit, the second inlet water quality probe including a second conductivity sensor and a second temperature sensor,
   a second worker bed having ion exchange media contained therein, and disposed to receive the second feedwater to be treated,
   a second worker probe disposed to measure at least one water parameter of water from the second worker bed, the second worker probe including a second worker conductivity sensor and a second worker temperature sensor,
   a second polisher bed having ion exchange media contained therein, and fluidly connected downstream from the second worker bed, a second polisher probe disposed to measure at least one polisher water parameter of water from the second polisher bed, the second polisher probe including a second polisher conductivity sensor and a second polisher temperature sensor, a second flow meter positioned at least one of upstream the second worker bed and downstream of the second polisher bed and configured to measure flow data of water introduced into the second local water treatment unit;

a second controller in communication with the second flow meter, the second inlet water quality probe, the second worker probe, and the second polisher probe, the second controller configured to receive the flow data from the second flow meter, the at least one measured inlet water parameter from the second inlet water quality probe, the at least one worker water parameter from the second worker probe, and the at least one polisher water parameter from the second polisher probe.

3. The system of claim 2, wherein the second water treatment unit is remote from and in communication with the server, the server further configured to receive from the second local water treatment unit, at least one of the flow data from the second flow meter, the at least one measured inlet water parameter from the second inlet water quality probe, the at least one worker water parameter from the second worker probe, and the at least one polisher water parameter from the second polisher probe.

4. The system of claim 3, wherein one of the second controller and the server is configured to determine at least one of a cumulative flow total of the second water treatment unit based on an aggregate of the flow data through the water second water treatment unit, a second billing cycle flow total based on the flow data during a second billing cycle through the second water treatment unit, a current exchange flow total based on the flow data during a current service period of the second worker bed, a second contaminant load based on the at least one inlet water parameter of the second feedwater, and a remaining capacity of the second local water treatment unit based at least on the second contaminant load.

5. The system of claim 4, wherein the local water treatment unit further includes an inlet pressure sensor disposed to monitor a pressure of the feedwater to the water treatment unit and an outlet pressure sensor disposed to monitor a pressure of the treated water from the water treatment unit, and wherein the controller is further configured to receive inlet pressure data from the inlet pressure sensor and outlet pressure data from the outlet pressure sensor and generate an alarm if a difference in the pressure of the feedwater relative to the pressure of the treated water is above a differential pressure setpoint.

6. The system of claim 5, wherein the local water treatment unit further includes a leak detect module disposed to detect a leak or moisture from the water treatment unit, and wherein the controller is further configured to generate an indication if the leak detection module detects moisture.

7. The system of claim 6, wherein the controller further comprises a Bluetooth® interface operatively configured to wirelessly transmit data over a personal area network.

8. A system for providing treated water, the system comprising:
a local water treatment unit including:
an inlet water quality probe disposed to measure at least one inlet water parameter of feedwater to be treated, the inlet water quality probe including a conductivity sensor and a temperature sensor configured to provide data utilized to apply an offset or calibration to data output from the conductivity sensor to reduce or eliminate an effect of temperature on the conductivity sensor readings, a worker bed having ion exchange media contained therein, and disposed to receive the feedwater to be treated, a worker probe disposed to measure at least one worker water parameter of water from the worker bed, the worker probe including a worker conductivity sensor and a worker temperature sensor configured to provide data utilized to apply an offset or calibration to data output from the worker conductivity sensor to reduce or eliminate an effect of temperature on the worker conductivity sensor readings, a polisher bed having ion exchange media contained therein, and fluidly connected downstream from the worker bed, a polisher probe disposed to measure at least one polisher water parameter of water from the polisher bed, the polisher probe including a polisher conductivity sensor and a polisher temperature sensor configured to provide data utilized to apply an offset or calibration to data output from the polisher conductivity sensor to reduce or eliminate an effect of temperature on the polisher conductivity sensor readings, a flow meter positioned at least one of upstream of the worker bed and downstream of the polisher bed and configured to measure flow data of water introduced into the local water treatment unit, and a controller in communication with the flow meter, the inlet water quality probe, the worker probe, and the polisher probe, the controller configured to receive the flow data from the flow meter, the at least one measured inlet water parameter from the inlet water quality probe, the at least one worker water parameter from the worker probe, and the at least one polisher water parameter from the polisher probe; and a server remote from and in communication with the local water treatment unit, the server configured to receive from the local water treatment unit, at least one of the flow data, the at least one measured inlet water parameter, the at least one worker water parameter, and the at least one polisher water parameter, at least one of the controller and the server further configured to:
determine a billing cycle flow total based on the flow data during a billing cycle through the local water treatment unit;
calculate a difference between the billing cycle flow total and a baseline volume of treated water expected to be provided during the billing cycle; and
determine a fee adjustment for providing the treated water based on the calculated difference between the billing cycle flow total and the baseline volume of treated water expected to be provided.

9. The system of claim 8, wherein the controller is further configured to determine a cumulative volume of treated water provided by the water treatment unit and determine a remaining service life of at least one of the worker bed and the polisher bed.

10. The system of claim 9, wherein the server is further configured to determine a schedule for servicing the local water treatment unit based on the determined remaining service life.

11. The system of claim 9, wherein the controller is further configured to linearly adjust raw conductivity readings from the inlet water conductivity sensor for temperatures different from a reference temperature of 25° C. by a temperature coefficient of 2.0% per degree C.

12. The system of claim 9, wherein the controller is further configured to linearly adjust raw conductivity readings from the worker conductivity sensor for temperatures different from a reference temperature of 25° C. by a temperature coefficient of 5.2% per degree C.

13. The system of claim 9, wherein the controller is further configured to linearly adjust raw conductivity readings from the polisher conductivity sensor for temperatures different from a reference temperature of 25° C. by a temperature coefficient of 5.2% per degree C.

* * * * *